(12) United States Patent
Gorfinkel et al.

(10) Patent No.: US 8,231,844 B2
(45) Date of Patent: Jul. 31, 2012

(54) METHOD AND DEVICE FOR MANIPULATING LIQUIDS IN MICROFLUIDIC SYSTEMS

(75) Inventors: Vera Gorfinkel, Stony Brook, NY (US); Evgeni A. Kabotyanski, Port Jefferson Station, NY (US)

(73) Assignee: The Research Foundation Of State University Of New York, Albany, NY (US)

( * ) Notice: Subject to any disclaimer, the term of this patent is extended or adjusted under 35 U.S.C. 154(b) by 919 days.

(21) Appl. No.: 11/975,887

(22) Filed: Oct. 22, 2007
(Under 37 CFR 1.47)

(65) Prior Publication Data
US 2009/0071833 A1  Mar. 19, 2009

(51) Int. Cl.
*G01N 15/06* (2006.01)
*G01N 33/00* (2006.01)
*G01N 33/48* (2006.01)

(52) U.S. Cl. ......... 422/502; 422/68.1; 422/100; 436/43; 436/180

(58) Field of Classification Search .............. 422/68.1, 422/100, 502, 503
See application file for complete search history.

(56) References Cited

U.S. PATENT DOCUMENTS

| 4,233,029 | A | * | 11/1980 | Columbus | 436/174 |
| 4,683,195 | A | | 7/1987 | Mullis et al. | 435/6 |
| 4,683,202 | A | | 7/1987 | Mullis et al. | 435/91 |
| 5,783,148 | A | | 7/1998 | Cottingham et al. | 422/56 |
| 6,057,149 | A | | 5/2000 | Burns et al. | 435/287.2 |
| 6,235,175 | B1 | | 5/2001 | Dubrow et al. | 204/453 |
| 6,271,040 | B1 | | 8/2001 | Buechler | 436/170 |
| 6,296,126 | B1 | * | 10/2001 | Peters | 210/456 |
| 6,447,661 | B1 | | 9/2002 | Chow et al. | 118/413 |
| 6,464,852 | B1 | | 10/2002 | Gorfinkel et al. | 204/600 |
| 6,475,362 | B1 | | 11/2002 | Gorfinkel et al. | 204/451 |
| 6,497,804 | B1 | | 12/2002 | Gorfinkel et al. | 204/603 |
| 6,517,234 | B1 | | 2/2003 | Kopf-Sil et al. | 366/340 |
| 6,533,914 | B1 | | 3/2003 | Liu | 204/601 |
| 6,541,274 | B2 | | 4/2003 | Nagle et al. | 436/180 |
| 6,551,836 | B1 | | 4/2003 | Chow et al. | 436/149 |
| 6,581,441 | B1 | | 6/2003 | Paul | 73/61.52 |
| 6,773,567 | B1 | | 8/2004 | Wolk | 204/604 |
| 6,821,485 | B2 | | 11/2004 | Beebe et al. | 436/180 |

FOREIGN PATENT DOCUMENTS

EP  101590171 B1  12/2003

OTHER PUBLICATIONS

Barry et al., "Microfluidics in biotechnology," *J Nanobiotechnol*, 2: 2 (2004).
Burns, M.A. et al., "An Integrated Nanoliter DNA Analysis Device", *Science*, 282: 484-487 (1998).

(Continued)

*Primary Examiner* — Brian J Sines
(74) *Attorney, Agent, or Firm* — Medlen & Carroll, LLP

(57) ABSTRACT

The present invention relates to microfluidic systems having components with specially designed and fabricated areas of enhanced and/or reduced capillarity (flow guides). The methods and devices of the present invention permit the bubble-less dispensing and mixing of small volumes of different liquids for subsequent incubation and/or detection of products of various biological reactions. Thus present invention is well-suited to applications such as polymerase chain reaction and capillary electrophoresis.

13 Claims, 19 Drawing Sheets

OTHER PUBLICATIONS

Coen "Chapter 15: The Polymerase Chain Reaction" in Ausubel et al., *Current Protocols in Molecular Biology*, John Wiley & Sons, 15.0.1-15.0.3 (2001).

Doig "Microfluidics technology goes mainstream" *Genetic Engineering News*, 25(2): 26-27 (2005).

Emrich et al, "Microfabricated 384-lane capillary array electrophoresis bioanalyzer for ultrahigh-throughput genetic analysis," *Analytical Chemistry*, 74: 5076-5083 (2002).

Fiorini et al. "Disposable microfluidic devices: fabrication, function and application" *Biotechniques* 38: 429-446 (2005).

Handique, K. et al., "Nanoliter-Volume Discrete Drop Injection and Pumping in Microfabricated Chemical Analysis Systems", *Solid-State Sensor and Actuator Workshop*, Hilton Head Island, South Carolina, Jun. 8-11: 346-349 (1998).

Kramer et al. "Enzymatic Amplification of DNA by PCR: Standard Procedures and Optimization" in Ausubel et al., *Current Protocols in Molecular Biology*, John Wiley & Sons, 15.1.1-15.1.14 (2001).

Lagally et al., "Monolithic Integrated PCR Reactor-CE System for DNA amplification and analysis to the single molecule limit," Poster 115, pp. 437-441, *2nd Annual IEEE-EMBS Special Topic Conference on Microtechnologies in Medicine and Biology*, Madison, WI (2002.

Lagally et al., "Fully intergrated PCR-capillary electrophoresis microsystem for DNA analysis," Lab Chip, 1(2):102-7 (2001).

Lagally et al., "Monolithic integrated microfluidic DNA amplification and capillary electrophoresis analysis system," *Senors and Actuators B*, 63:138-146 (2000).

Lagally et al., "Single-molecule DNA amplification and analysis in an integrated microfluidic device," *Analytical Chemistry*, 73:565-570 (2001).

Lederman "Microfluidics: Big things in narrow channels" *BioTechniques*, 37(1): 20-21 (2004).

Northrup et al., "DNA Amplification with a Microfabricated Reaction Chamber", *Proceedings of the 7th International Conference on Solid-State and Actuators*, Yokohama, Japan, pp. 923-926 (1993).

Schmalzing et al. "DNA typing in thirty seconds with a microfabricated device," *Proc Natl Acad Sci USA*, 94: 10273-10278 (1997).

Smith et al. "Capillary Electrophoresis of DNA" in Ausubel et al., *Current Protocols in Molecular Biology*, John Wiley & Sons, 2.8.1-2.8.17 (2004).

Thorsen, "Microfluidic tools for high-throughput screening," *BioTechniques*, 36: 197-199 (2004).

\* cited by examiner

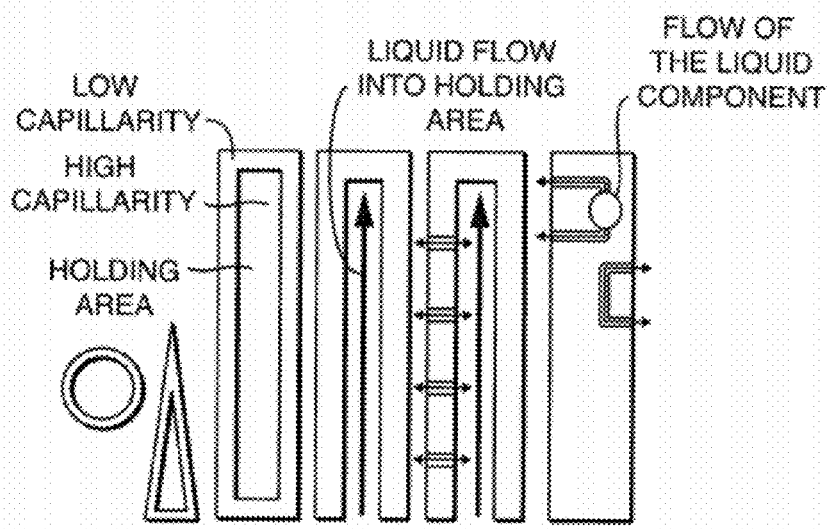
FIG. 3K
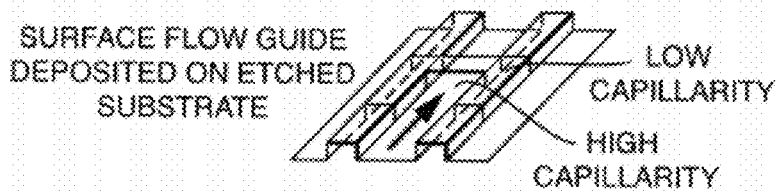
FIG. 3L
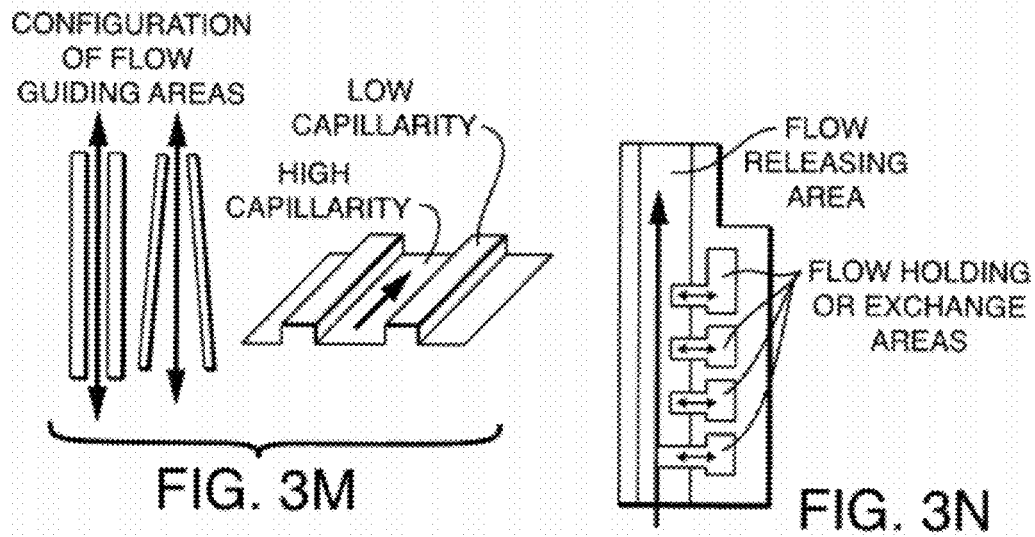
FIG. 3M
FIG. 3N

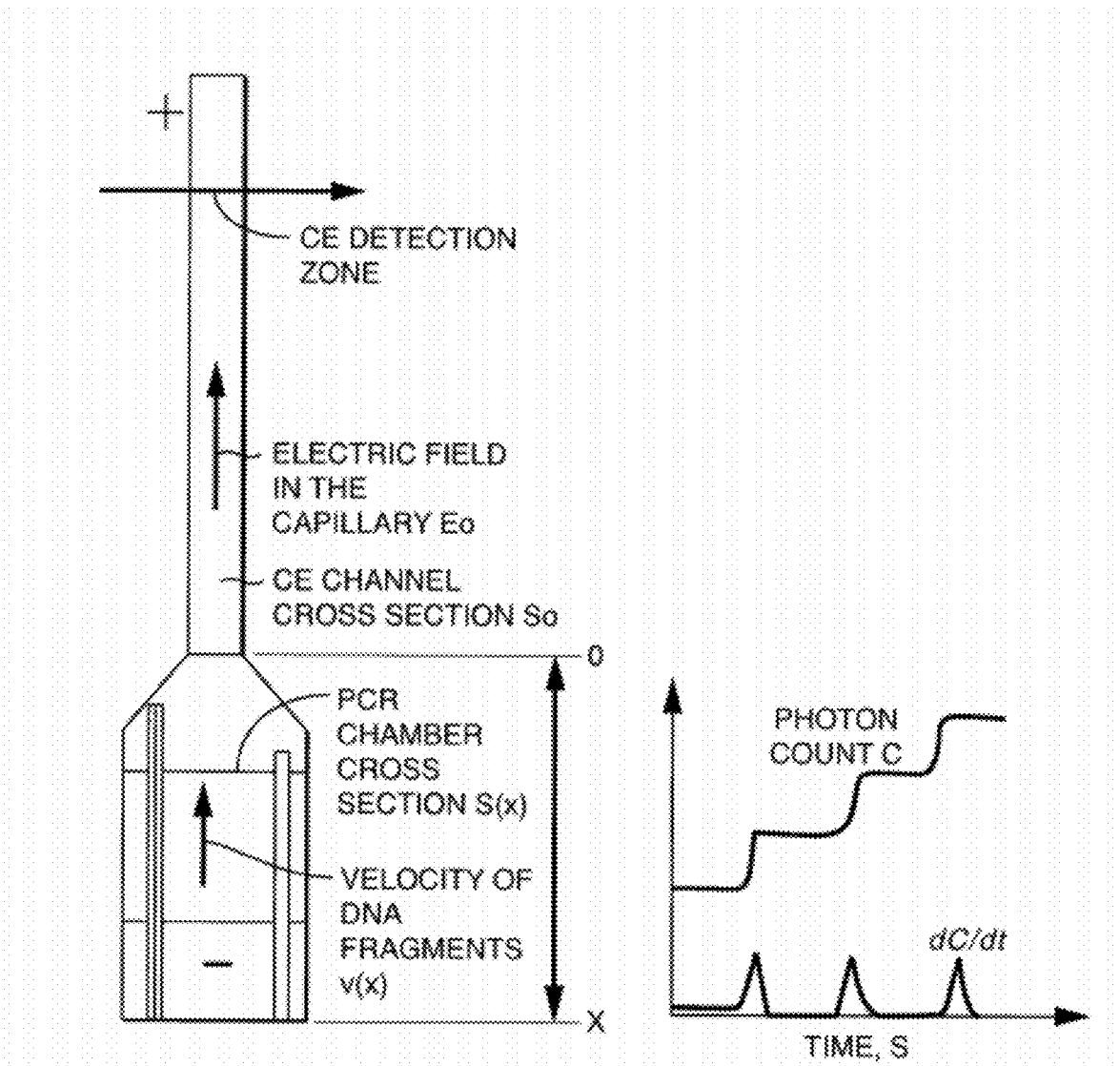

METHOD AND DEVICE FOR MANIPULATING LIQUIDS IN MICROFLUIDIC SYSTEMS

This application claims the benefit of U.S. Provisional Application No. 60/546,235, filed on Feb. 20, 2004, herein incorporated by reference.

TECHNICAL FIELD

The present invention relates to methods and devices suitable for use in various biotechnology applications, such as those involving polymerase chain reaction and/or capillary electrophoresis. In particular the present invention provides microfluidic systems having one or more components with enhanced or reduced capillarity.

BACKGROUND

Versatile microsystems for DNA amplification with polymerase chain reaction (PCR) and DNA analysis with capillary electrophoresis (CE) have become increasingly popular since such devices were first described (Northrup et al., "DNA amplification with a microfabricated reaction chamber," Proceedings of the $7^{th}$ International Conference on Solid-State Sensors and Actuators, Yokohama, Japan, pp. 923-926, 1993). These instruments are typically manufactured as sandwich chips or wafers from silicon, glass, or plastic substrates, by using scalable microfabrication techniques originated in the semiconductor industry. Microfabricated devices permit limitations of conventional PCR (long assay times, large and/or expensive volumes of reaction components, etc.) to be overcome. Examples of recent designs include fully integrated PCR-CE microfluidic devices (See, e.g., Lagally et al., Sensors and Actuators B, 63:138-146, 2000; Lagally et al., Analytical Chemistry, 73:565-570, 2001; Lagally et al., Lab on a Chip, 1:102-107, 2001; and Lagally et al., "Monolithic integrated PCR reactor-CE system for DNA amplification and analysis to the single molecule limit," $2^{nd}$ Annual IEEE-EMBS Special Topic Conference on Microtechnologies in Medicine and Biology, Madison, Wis., 2002), and 384-lane CE arrays (Emrich et al., Analytical Chemistry, 74:5076-5083, 2002).

Further progress in design, development and use of on-chip DNA analysis technology is hampered, however, by difficulties derived from inherent properties of microfluidics and from the handling of microfluidic devices. Problems occur for instance when connecting to macrodevices, loading very small volumes, and mixing several components. When using the devices of the prior art, these steps frequently result in air encapsulation or forming of air bubbles, which in turn clogs the microfluidic channels leading to loading disturbances and contamination of samples and reagents or reagent mixtures. Prior to the development of the present invention, this problem was addressed by employment of various additional precautionary devices (e.g., vacuums, pumps, microfluidic valves and vents) that have made the technology less versatile and more expensive. Other microfluidic systems of the prior art have addressed the air bubble problem by using capillaries containing filaments that can be loaded by micropipette, microelectrode, etc. (Brown and Flaming, *Advanced Micropipette Techniques for Cell Physiology*, Sutter Co., 2001). Although the use of the capillary with filament structure allows one to fill the capillary with more than one liquid component without the introduction of air bubbles, this design results in the sequential loading of the capillary, and difficulties in mixing the different liquid components. Thus what is needed in the art, are less expensive and cumbersome microfluidic tools that permit bubble-less liquid loading, as well as complete mixing of different liquids.

SUMMARY

The present invention relates to methods and devices suitable for use in various biotechnology applications, such as those involving polymerase chain reaction and/or capillary electrophoresis. In particular the present invention provides microfluidic systems having one or more components with enhanced or reduced capillarity.

The present invention provides microfluidic devices comprising one or more microfluidic vessel(s), wherein each of the microfluidic vessel(s) comprise walls and at least one flow guide contained therein, for controlling the flow of liquids within the microfluidic vessel(s). In some preferred embodiments, the at least one flow guide comprises a holding flow guide that extends toward but does not contact a distal wall of the microfluidic vessel(s), and wherein the controlling comprises delaying the flow of a liquid toward the distal wall (by directing the flow of a liquid to a position measurably short of said distal wall). In additional preferred embodiments, the at least one flow guide further comprises a releasing flow guide that extends toward and contacts a distal wall of the microfluidic vessel(s), and wherein the controlling comprises hastening the flow of a liquid toward the distal wall (by directing the flow of a liquid to a position contacting said distal wall). In some preferred embodiments, the at least one flow guide comprises an area within the microfluidic vessel(s) having reduced capillarity, and/or areas within the microfluidic vessel(s) having enhanced capillarity. In some embodiments, the at least one flow guide is a structural flow guide and/or surface flow guide. In a subset of these embodiments, the surface flow guide comprises a hydrophobic material deposited within the microfluidic vessel(s). In some preferred embodiments, the hydrophobic material comprises trichlorosilane, and the microfluidic vessel(s) comprises a glass substrate. In further embodiments, the flow guide is a hybrid structural/surface flow guide.

In addition, the present invention provides microfluidic systems comprising the microfluidic devices described above, and a thermal cycling component. A subset of these microfluidic systems, further comprise a capillary electrophoresis component and at least three electrodes, and/or one or more detection component(s).

Moreover, the present invention provides automated loading systems, comprising: a stationary loading station comprising a sample-loading capillary tube, a reagent-loading capillary tube, and a guillotine for cleaving used portions of the tubes; and a movable programmable stage for positioning the microfluidic devices described above, and a sample tray in juxtaposition to the tubes, for dispensing a sample onto the holding flow guide and for dispensing reagents onto the releasing flow guide of the microfluidic vessel(s). In some preferred embodiments, the movable programmable stage is configured to move both horizontally and vertically.

Also provided by the present invention are methods for loading and/or unloading a microfluidic device suitable for minimizing reagent and/or sample contamination, comprising: a) providing a microfluidic device comprising one or more microfluidic vessel(s), wherein the microfluidic vessel(s) comprise walls with two or more ports, a holding flow guide and a releasing flow guide, wherein the two or more ports comprise a sample port and a reagent port, and wherein the releasing flow guide extends toward and contacts a distal wall of the microfluidic vessel(s), while the holding flow guide extends toward but does not contact a distal wall of the microfluidic vessel(s); b) dispensing a sample through the sample port onto the holding flow guide; and c)dispensing a reagent through the reagent port onto the releasing flow guide. In particularly preferred embodiments, the sample comprises a smaller volume than does the reagent. In further embodiments, when the two or more ports further comprise a venting or sampling port, the method further comprises releasing any air contained within the microfluidic vessel(s). In some embodiments, when the two or more ports further comprise a venting or sampling port, the method further comprises removing a portion of the liquid contained with the microfluidic vessel(s).

DESCRIPTION OF THE DRAWINGS

FIG. 7B is a schematic of a single channel of the monolith multi-capillary PCR/CE array shown in FIG. 7A.

FIG. 7C is a graph showing that the photon count observed at the CE detection zone of the channel shown in FIG. 7B is expected to change in time as a step-like function.

DEFINITIONS

Figure 1:
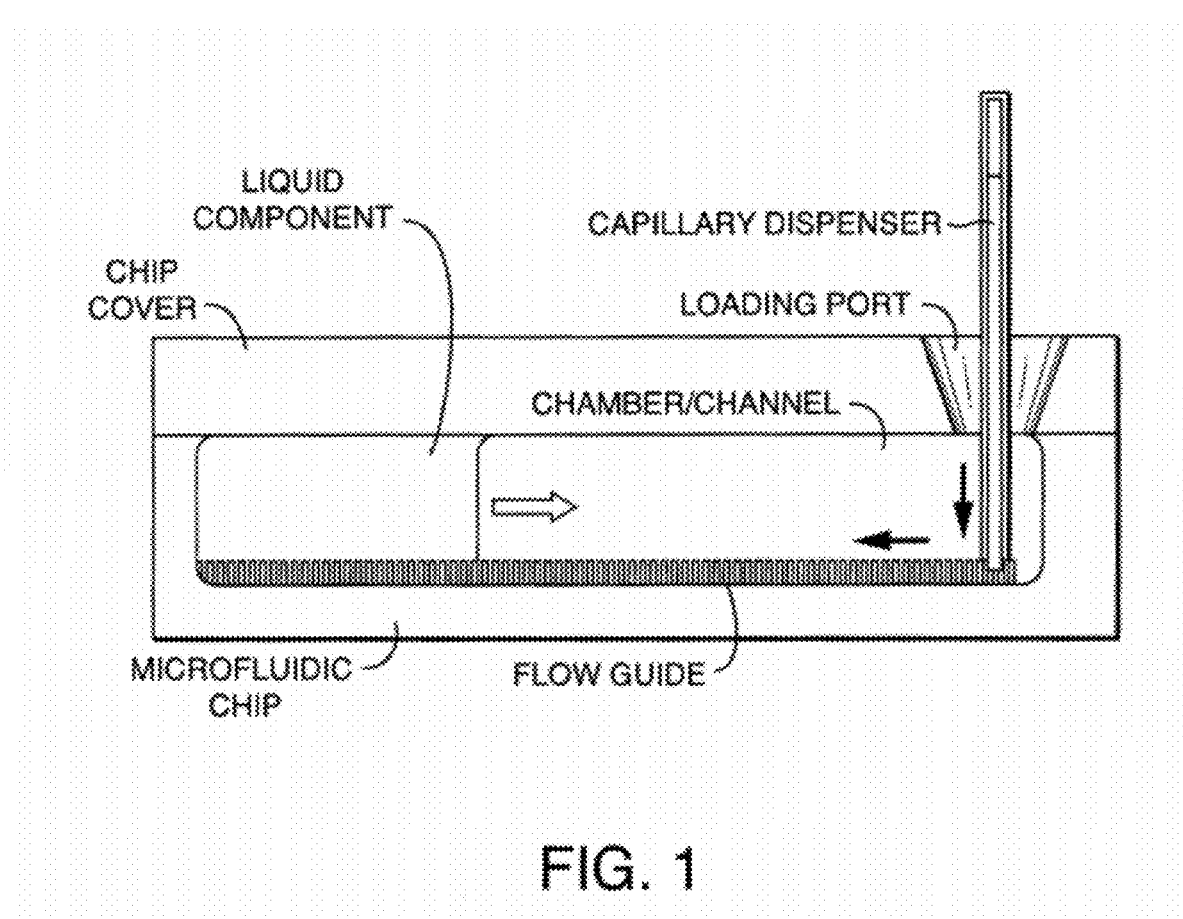
FIG. 1 illustrates the loading of a liquid into a flow guide containing chamber or channel of a microfluidic chip with the use of a pipette or capillary dispenser.

To facilitate an understanding of the present invention, a number of terms and phrases are defined below:

As used herein, the term "biological reaction" refers to reactions involving biomolecules such as proteins (e.g., polymerases, nucleases, etc.), and/or nucleic acids (both RNA and DNA).

"Biological samples" are those containing biomolecules, such as proteins, lipids, and/or nucleic acids. The sample may be obtained from a microorganism (e.g., bacterial culture), a plant or an animal, including humans (e.g., blood, urine, etc.). Optionally, the sample may have been subjected to purification (e.g., extraction) or other treatment. Biological reactions require some degree of biocompatability with the device. That is to say, the reactions ideally should not be substantially inhibited by the characteristics or nature of the device components.

As used herein, the term "reagent" refers to one or more substances that are useful in biochemical analysis or synthesis. Similarly, the terms "reagents," "reagent mixture," "reagent cocktail" and "master mix" refer to a combination of such substances. For instance, a PCR reaction cocktail generally comprises a buffer, dNTPs, $MgCl_2$ and a thermostable polymerase, in the absence of a sample (e.g., liquid suspected to contain a nucleic acid template of interest).

As used herein, the term "microfluidics" refers to a multidisciplinary field comprising physics, chemistry, engineering and biotechnology, that studies the behavior of fluids at the microscale and mesoscale level, and to the design of systems in which such small volumes of fluids are used. Such "lab-on-a-chip" technology (See, e.g., Barry and Ivanov, J Nanobiotechnol, 2:2, 2004; and Thorsen, BioTechniques, 36:197-199, 2004, herein incorporated by reference) is based on the transport of nanoliter or picoliter volumes of fluids through microchannels within a glass or plastic device (e.g., chip). The behavior of fluids at the microscale level differs from "macrofluidic" behavior in that factors such as surface tension, energy dissipation, and electrokinetics begin to dominate the system.

As used herein, the terms "capillarity" and "capillary action" refer to phenomenon in which the surface of a liquid is observed to be elevated (or depressed) where it comes into contact with a solid. For example, the surface of water in a clean drinking glass is seen to be slightly higher at the edges, where it contacts the glass, than in the middle. Capillarity refers to the effects of two opposing forces: adhesion, the attractive (or repulsive) force between the molecules of a liquid and those of a vessel, and cohesion, the attractive force between the molecules of a liquid. The forces of adhesion act to maximize the surface area of a liquid. Adhesion causes water to wet a glass container and thus causes the water's surface to rise near the container's walls. If there were no forces acting in opposition, the water would creep higher and higher on the walls and eventually overflow the container. In contrast, the forces of cohesion act to minimize the surface area of the liquid. When the cohesive force acting to reduce the surface area of a liquid becomes equal to the adhesive force acting to increase the surface area, equilibrium is reached and the liquid stops flowing. In some liquid-solid systems, (e.g., mercury and glass, water and polyethylene plastic, etc.) the liquid does not wet the solid, and its surface is depressed where it contacts the solid.

As used herein the term "port" refers to an opening in a microfluidics device through which liquid(s) or gases are placed within or removed from a microchannel or microchamber.

As used herein the terms "channels," "chambers" and "vessels," refer to pathways through a medium (e.g., silicon, glass, etc.) that allow for movement of liquids and/or gases. In particular, "microfluidic channels" are channels measured in microns and configured so as to accommodate micro-, submicro- or nano-liter volumes. While it is not intended that the present invention be limited by precise dimensions of the channels or precise volumes, illustrative ranges for microfluidic channels are as follows: the channels can be between 0.35 and 50 µm in depth (preferably 20 mm) and between 50 and 1000 µm in width (preferably 500 µm), with volumes in the range (calculated from their lengths) of between approximately one (1) and 1000 nanoliters (more typically between 10 and 100). The vessels of the present invention are not limited to these exemplary ranges, as the inventors contemplate that suitable dimensions comprise any measurements that provide the desired capillary effect. An "electrophoresis channel" is a channel substantially filled with a material that aids in the differential migration of biomolecules.

As used herein, the term "wall," when used in relation to a micro- or microfluidic vessel, micro- or microfluidic chamber, micro- or microfluidic channel, or capillary channel of the invention, relates to an area or region of such vessel, chamber or channel that may interface with a liquid disposed within such a vessel, chamber, channel or capillary. Where a liquid tends to flow under capillary pressure toward a given region of such vessel, chamber or channel, the walls in that region are said to have "enhanced capillarity" with respect to the walls in the region or regions out of which the same liquid tends to flow. Where an amount of liquid tends to flow under capillary pressure away from a given region of such vessel, chamber or channel, the walls in that region are said to have "reduced capillarity" with respect to the walls in the region into which the same amount of liquid tends to flow. The term "distal wall" as used herein, refers to a region of such vessel, chamber or channel furthest away from the loading ports of the vessel, chamber or channel.

As used herein, the term "flow guide" refers to a configuration within a microfluidic vessel for directing the flow of a liquid deposited therein. A flow guide is constructed by providing each of the several inner regions of a vessel, chamber or channel with walls of enhanced and/or reduced capillarity, consistent with the flow plan for the desired microfluidic device or system. Thus, the term "flow guide" refers to any portion of any vessel, chamber or channel of the invention that is so constructed.

As used herein, a "structural flow guide" means a flow guide wherein enhanced and/or reduced capillarity is conferred upon the walls that comprise such flow guide by modifying the wall with cracks, slits, notches, grooves, flutes, or other structures (concavity, convexity or combinations thereof) which may be etched or carved thereon or deposited, plated or coated thereon.

As used herein, a "surface flow guide" means a flow guide wherein enhanced and/or reduced capillarity is conferred upon the walls that comprise such flow guide by fabricating the wall with materials whose surface forms either a hydrophilic wall to enhance capillarity or a hydrophobic wall to reduce capillarity.

The term "hybrid structural/surface flow guide" refers to a flow guide having elements of both structural and surface flow guides. Enhanced and/or reduced capillarity is conferred upon the walls that comprise the hybrid flow guides of the present invention by modifying portion(s) of the wall with a concavity, convexity or combinations thereof, and by fabricating portion(s) of the wall with hydrophilic and/or hydrophobic surfaces.

As used herein, the terms "reactor" or "processor" refers to a microfluidic structure comprising a void of a defined physical volume (e.g., chamber) or to a combination of voids in which biological or chemical reactions take place.

As used herein the terms "chip" and "biochip" refer to microscale systems for bioanalysis based on integrated circuit technology. Biochips include molecular microarrays (gene chips, protein chips, small molecule chips), microfluidics systems (lab-on-a-chip), and fiber-optic-based arrays.

As used herein, the term "nucleic acid amplification" refers to methods for increasing the concentration of a nucleic acid, and in particular, the concentration of a particular piece of nucleic acid. A preferred technique is known as the "polymerase chain reaction" or "PCR" and is well known in the art (See, e.g., Ausubel et al. (ed.), in *Current Protocols in Molecular Biology*, John Wiley & Sons, 15.0.1-15.0.3 and 15.1.1-15.1.14, 2001, herein incorporated by reference). Mullis et al. (U.S. Pat. Nos. 4,683,195 and 4,683,202) describe a method for increasing the concentration of a segment of target sequence in a mixture of genomic DNA without cloning or purification. This process for amplifying the target sequence consists of introducing a molar excess of two oligonucleotide primers to the DNA mixture containing the desired target sequence. The two primers are complementary to their respective strands of the double-stranded sequence. The mixture is denatured and then allowed to hybridize. Following hybridization, the primers are extended with polymerase so as to form complementary strands. The steps of denaturation, hybridization, and polymerase extension can be repeated as often as needed to obtain are relatively high concentration of a segment of the desired target sequence. The length of the segment of the desired target sequence is determined by the relative positions of the primers with respect to each other, and therefore, this length is a controllable parameter. Because the desired segment of the target sequence becomes the dominant sequences (in terms of concentration) in the mixture, the sequence is said to be "PCR-amplified."

As used herein the terms "capillary electrophoresis" and "CE" refer to a technique for separating molecules of a sample (or products of a reaction) according to their molecular weight, by placement of a sample in capillary channel, which is then subjected to a high voltage (See, e.g., Ausubel et al. (ed.), in *Current Protocols in Molecular Biology*, John Wiley & Sons, Inc., 2.8.1-2.8.17, 2004, herein incorporated by reference).

DESCRIPTION OF THE INVENTION

The presently claimed invention comprises methods and devices for manipulating small volumes of liquids in microfluidic systems having areas of prefabricated non-uniform capillarity. In some preferred embodiments, the microfluidic systems (e.g., assembly, chip, plate, etc.) comprising microfluidic reactors, channels, chambers, ports, etc. having specially designed and constructed sectors of enhanced (e.g., super capillary flow guides or ducts) and/or reduced capillarity (e.g., anti-capillary flow guides or ducts). In some embodiments, the methods comprise discrete steps to be accomplished in a defined order for manipulation of multiple liquids, such as a specific order of filling or loading the liquids (e.g., reagents or samples) into the channels or chambers of the microfluidic systems. For instance, to prevent air encapsulation, the dispenser tip (e.g., pipette or syringe needle) should touch only the flow guide, and not the rest of the channel during the loading step. The constructive (e.g., microfluidic devices having flow guides) and the operational (e.g., methods of using microfluidic devices) solutions of the present invention make possible the bubble-less dispensing, loading, mixing, reacting, and separating, etc., of small volumes of liquids within the channels of various microfluidic systems (FIG. 1). The methods and devices described herein can be used for manipulation and analysis of nucleic acid or protein samples by various routine molecular biology techniques (e.g., real-time PCR, capillary electrophoresis, etc.).

Figure 2A:
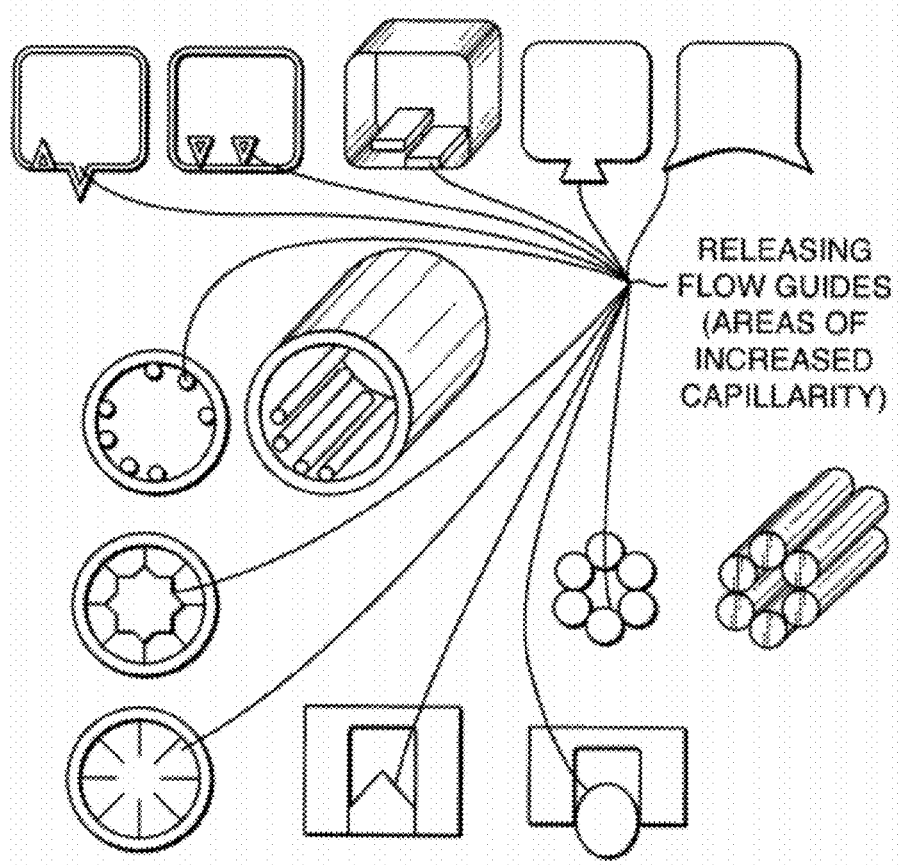
FIG. 2A illustrates a variety of microfluidic vessel (e.g., chamber or capillary channel) configurations in saggital cross-section. Lines indicate areas of increased capillarity (flow guides).
Figure 4:
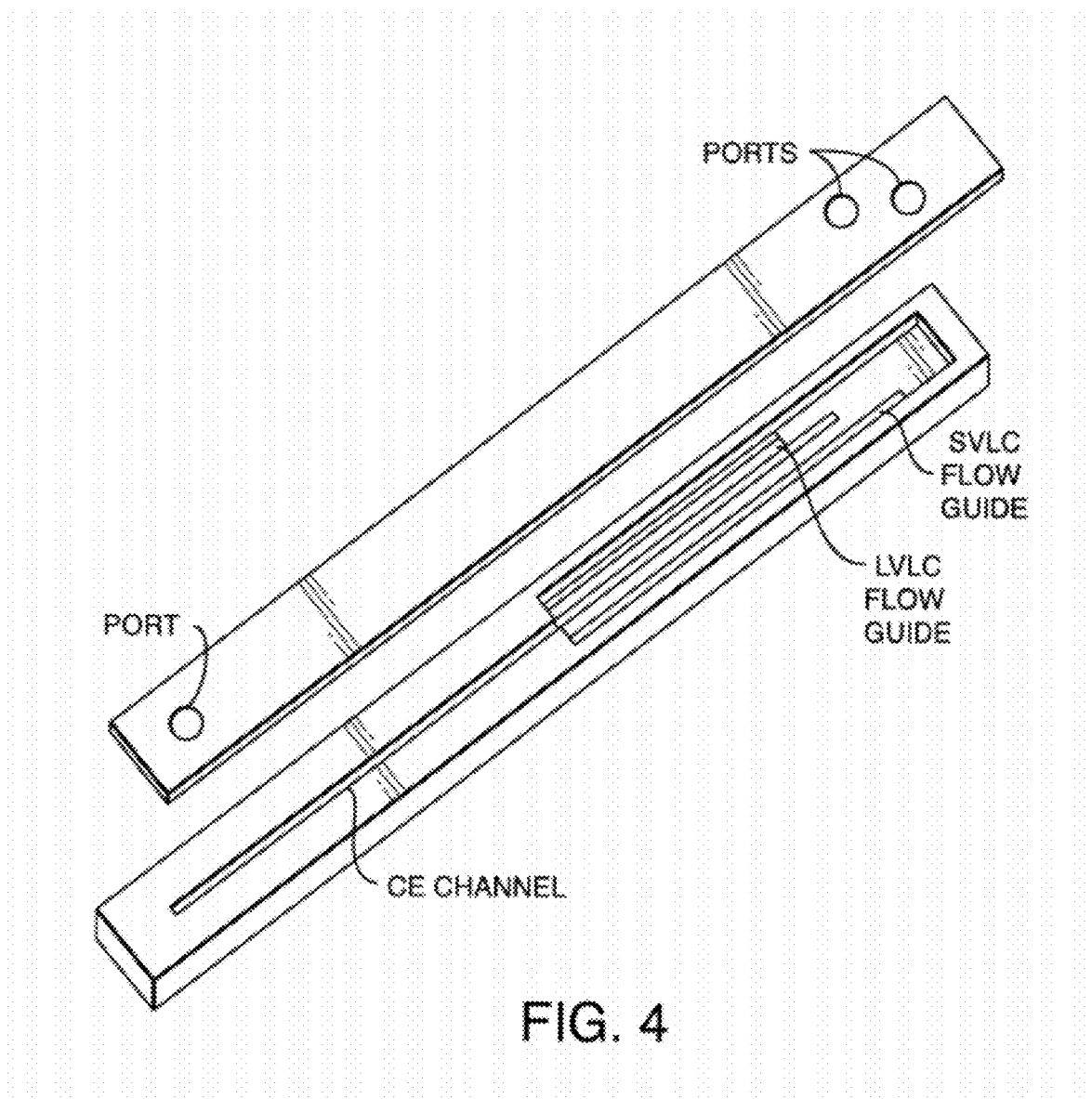
FIG. 4 is a schematic of a microfluidic chamber with three openings, including a loading port for reagents (larger volume), a loading port for a sample (smaller volume) as well as a sampling or venting port.

A multitude of microfluidic channels, chambers, capillaries, or other cavities, which have pointed non-uniformities (increase or decrease) in capillarity across their saggital perimeter (FIG. 2A) are suitable for use with the methods and devices of the present invention. The non-uniformities comprise narrow sectors bearing enhanced (or reduced) capillarity within or along walls of a microfluidic channel, relative to the rest of the channel wall. The non-uniformities comprise structures, formations, profiles, or compositions (FIG. 2A-B, and FIG. 3A-O), termed flow guides (e.g., sub-capillaries, co-capillaries, super-capillaries; or anti-capillaries, anti-guides). Multiple liquids of interest are loaded into the channels through individual (FIG. 2B) or common loading ports (FIG. 2C, and FIG. 4). The flow guides permit the uninterrupted flow of liquids of interest, thereby preventing the formation of air bubbles that can clog microfluidic channels during loading, mixing, reacting, and/or separating.

Flow Guides

Figure 2B:
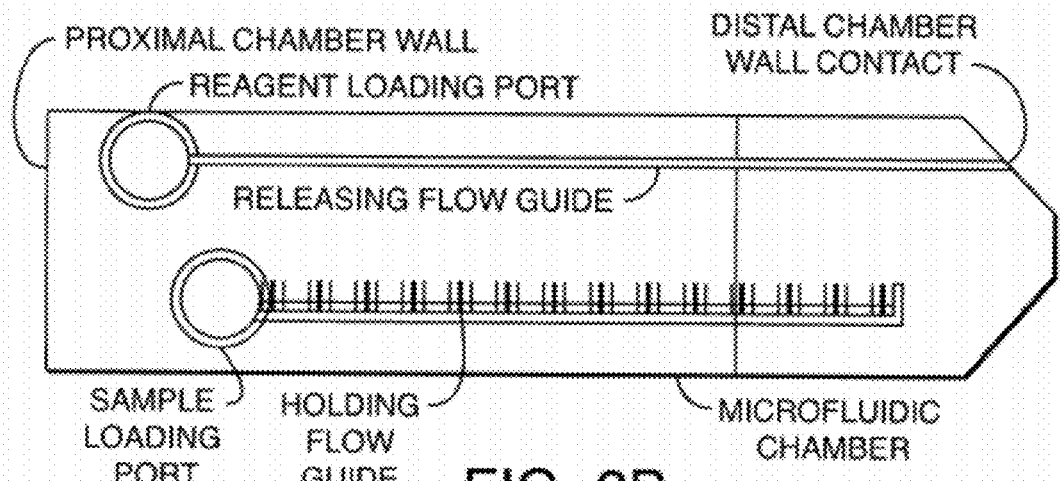
FIG. 2B illustrates a microchannel with two loading ports and flow guides for introduction and mixing of two different liquids.

The microfluidic channels of the present invention comprise one or more flow guides that are positioned parallel to each other or are joined in any suitable manner (e.g., V-like, Y-like, star-like, etc.). In some embodiments, the flow guides are of equal or varying length, and span the whole length of the microfluidic chamber or are shorter than the latter at one or both ends (FIG. 2B). In a preferred embodiment, a flow guide that spans the length of the microfluidic chamber and makes contacts with the chamber's wall at one of the ends serves as a duct. The duct delivers fluid first to the end of the chamber where the fluid contacts the wall before filling the chamber by capillary action. This configuration permits the controlled bubble-free filling of the microfluidic chamber with a large volume liquid component (e.g., reagents). In contrast, a flow guide that does not contact either of the microfluidic chamber's end walls serves as a holding area for a small volume (e.g., sample) of liquid loaded onto it. The dual flow guide configuration comprising a full length guide and a partial length guide provides a means for the gradual distribution and mixing of the small volume liquid with the large volume liquid when the large volume liquid is loaded into the microfluidic chamber (FIG. 2B and FIG. 3K).

Figure 3A:
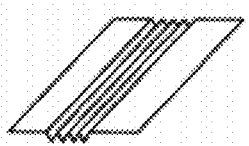
FIG. 3A-N illustrates a variety of flow guides formed by combining areas of enhanced and reduced capillarity, for use with the microfluidic systems of the present invention.
Figure 3B:
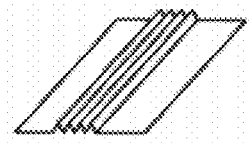
FIG. 3O illustrates a preferred microfluidic vessel comprising both a holding flow guide and a releasing flow guide.
FIG. 3P illustrates the loading of two different liquids in a microfluidic vessel comprising a chip cover.
Figure 3C:
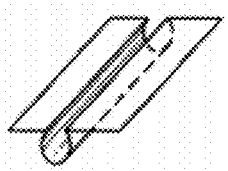
Figure 3D:
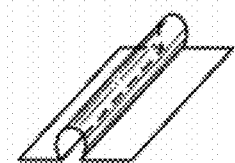
Figure 3E:
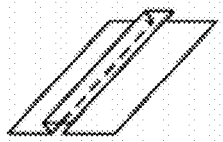
Figure 3F:
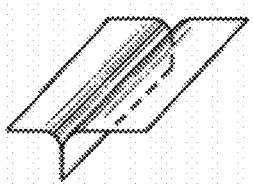
Figure 3G:
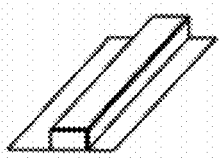
Figure 3H:
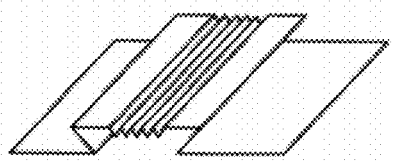
Figure 3I:
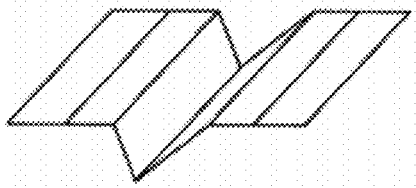
Figure 3J:
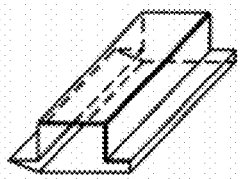
Figure 3O:
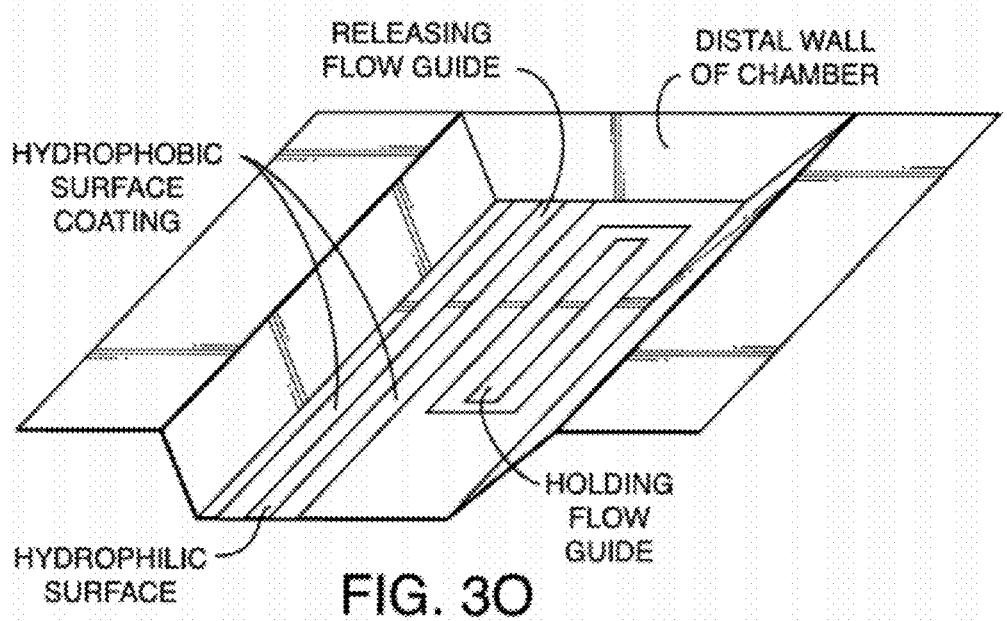
Figure 3P:
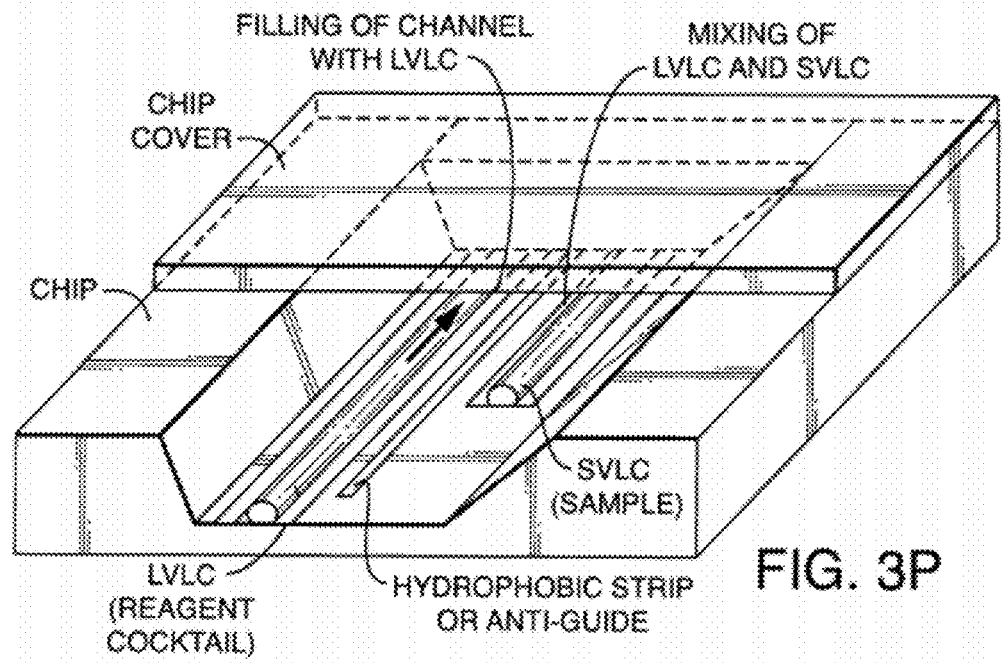

Various flow guide configurations are suitable for use with the present invention, including but not limited to: guides with etched or carved cracks, slits, notches, grooves, flutes (e.g., FIG. 3A, FIG. 3C, FIG. 3F, and FIG. 3I); guides with attached, soldered or etched (micro-) filaments, tubes, capillaries, fibers, ridges, blades, edges (e.g., FIG. 3B, FIG. 3D, and FIG. 3E); guides with regions of deposited, plated, or coated material(s) having extra high capillarity, such as micro- or nanoparticles (e.g., FIG. 3G, FIG. 3H, and FIG. 3I); guides with features formed by protruding or invaginating edges of sandwich layers (e.g., FIG. 3J); guides with regions of processed or altered cavity surfaces (e.g., a strip on the channel wall created by laser blasting, or mechanical surface processing, such as sanding, scratching, etc.); and guides with combinations of the above structures or features (e.g., FIG. 3H and FIG. 3I). For guides with deposits, plates or coats of high capillarity material, the micro- or nanoparticle materials are spheres/beads, tubes, tips, edges, or micro-cracks. In addition, suitable flow guide configurations include various profile geometries in cross-section (round, oval, triangular, rectangular, trapezoid, and polygon shape) and in length (cylinder, cone, prism, parallelepiped, polyhedron, pyramid, etc.) as shown in FIG. 2A and FIG. 3, and can vary in shape or size along its length in shape or size. In some embodiments, the flow guides are straight, while in others they are curved (sine-wave, spiral, etc.), with appendices, or crisscrosses (net-like or comb-like) (FIG. 2C). In further embodiments, the flow guides are a combination of the above types, shapes, geometries, and sizes (e.g., FIGS. 3H and 3I). The present invention also provides flow guides whose capillarity varies along or across itself. Likewise in some embodiments, the amount of liquid that a flow guide can accommodate as the liquid flows along or is held by the guide differs along its length (or between different flow guides). Flow guides in microfluidic chambers or channels are formed by a variety of technologies, including but not limited to, etching, engraving, carving, press-forming (mold pressing), extrusion, laser burst, laser cutting, film deposition, soldering/attaching, or forging/drawing.

Some preferred embodiments of the present invention comprise surface or flat flow guides that are created on a chip by forming and combining areas of enhanced (hydrophilic) and reduced (hydrophobic) capillarity. In some particularly preferred surface flow guides, the areas of reduced capillarity surround areas of enhanced capillarity (FIG. 3K). Depending upon their design, the surface flow guides are suitable for performing a sample holding function and/or a chamber filling function. In order to ensure mixing of liquid components in the chamber, some flow guides comprise openings in their reduced capillarity (hydrophobic) areas (FIG. 3N).

Microfluidic Chambers/Channels

Figure 5A:
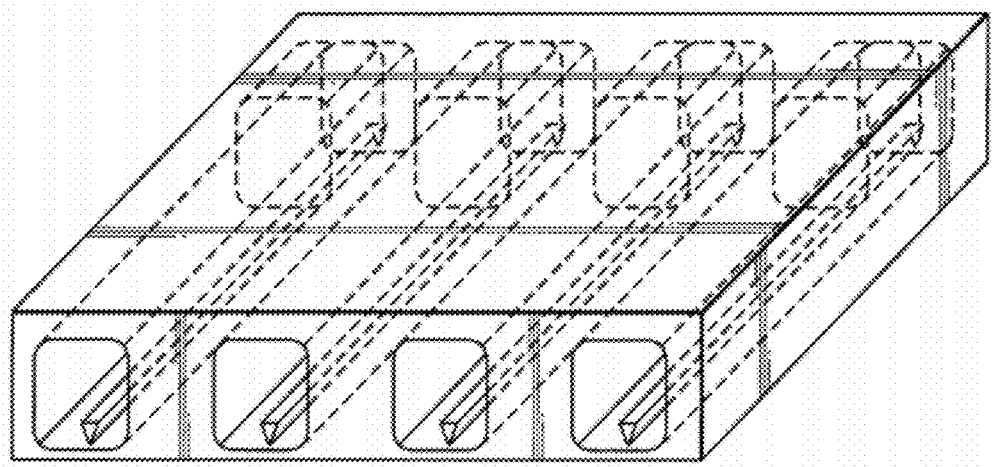
FIG. 5A is a schematic of a microfluidic vessel with multiple chambers assembled from multiple capillary tubes.
Figure 5B:
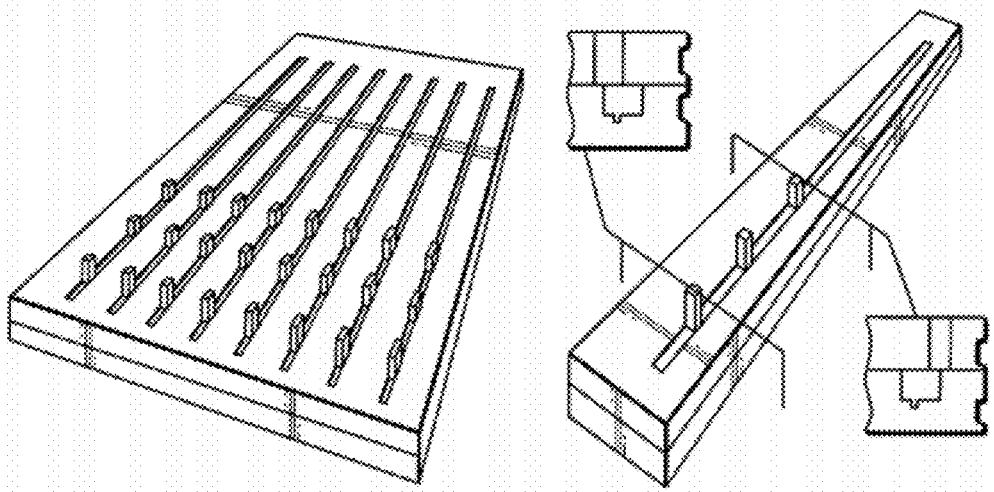
FIG. 5B illustrates a microfluidic vessel with multiple chambers produced with scalable microfabrication techniques including etching of glass, silicon, plastic, or combinations thereof (e.g., plate).
Figure 6:
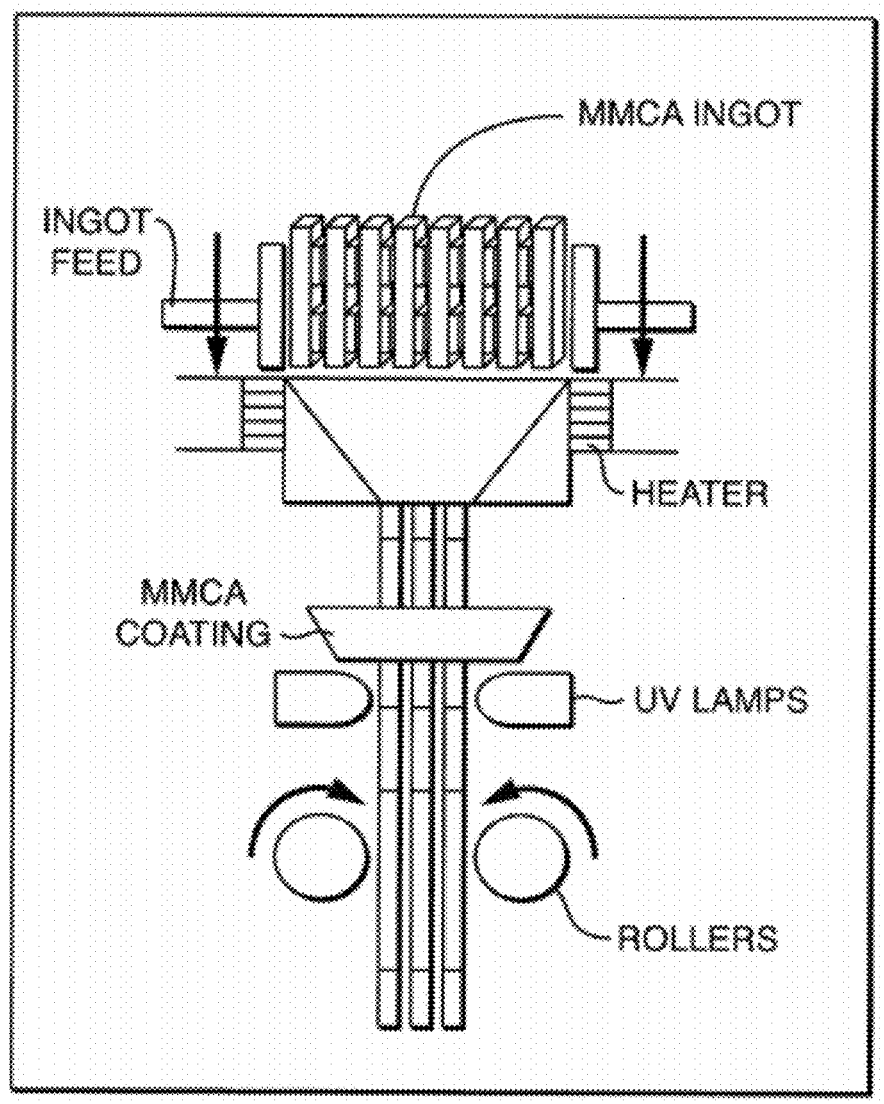
FIG. 6 illustrates a preferred fabrication process suitable for production of multi-capillary PCR/CE arrays of the present invention.
Figure 6A:
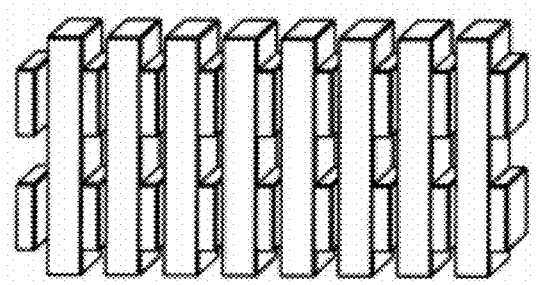
Figure 7A:
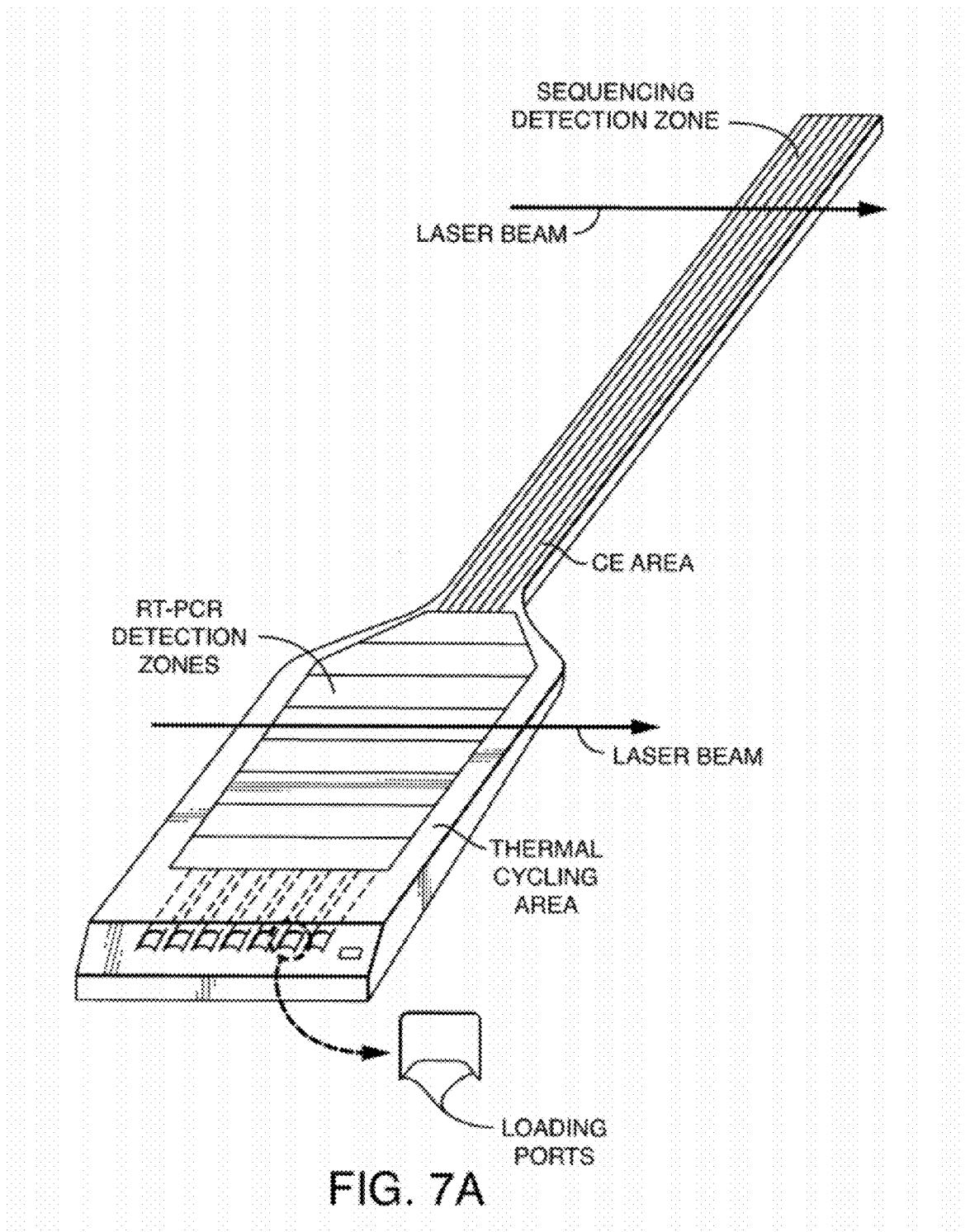
FIG. 7A illustrates a monolith multi-capillary PCR/CE array in which each channel has a non-uniform channel cross-section.
Figure 8:
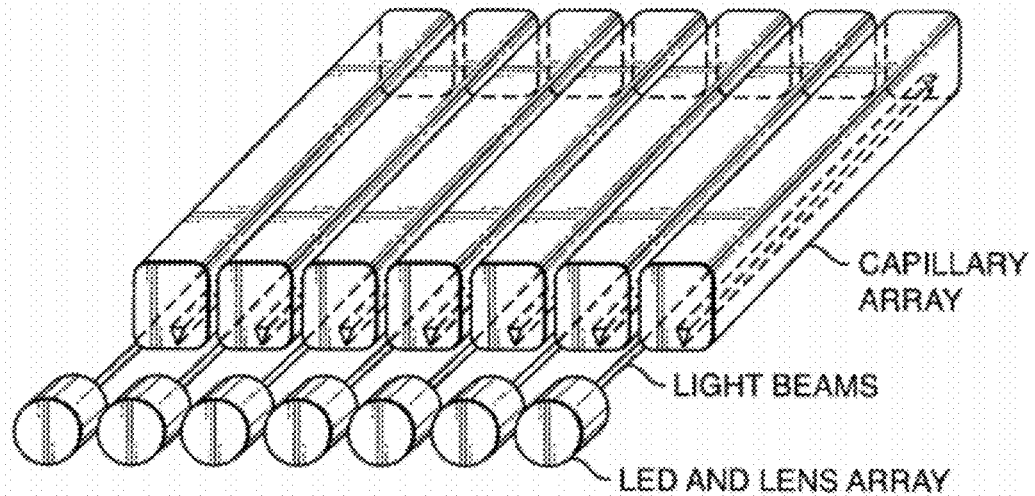
FIG. 8 illustrates the use of pre-fabricated optics with the microfluidic chambers of the present invention.

Microfluidic chambers or channels suitable for use with the present invention include single channel devices, as well as multi-channel arrays. In some embodiments, the channels are assembled from one or multiple capillary tubes (FIG. 5A) or prefabricated glass frames, or are manufactured with scalable microfabrication techniques including etching of glass, silicon, plastic, or hybrid chips or plates (FIG. 5B). Additional suitable microfabrication techniques include but are not limited to carving, engraving, sand blasting, laser bursting, and laser cutting of an appropriate channel material. In further embodiments, the channels are produced by extrusion through a draw plate, compaction (mold pressing), forging of prefabricated glass ingots (FIG. 6), or combinations of such techniques.

The microfluidic channels of the present invention may comprise a hydrophobic coating of any desired geometry on the inside and/or outside of the channel. Suitable microfluidic channel configurations include various profile geometries at cross-section (round, oval, triangular, rectangular, trapezoid, and polygon shape) and/or along its length (cylinder, cone, prism, parallelepiped, polyhedron, pyramid, etc.), and can vary somewhat in length and volume. In some preferred embodiments, the microfluidic devices comprise metal of various shapes, thicknesses, sizes and positions, which function for instance as electrodes, heaters, or sensors. In further embodiments, the microfluidic devices comprise one or more additional components such as semiconductors, which function as thermal pumps (heater and/or cooler), pre-fabricated optics (lenses, filters, dichroic mirrors, prisms, optical waveguides, or prefabricated mechanical parts (stirrers, etc.).

Exemplary Methods for Using a Microfluidic Device With Flow Guide

Figure 9:
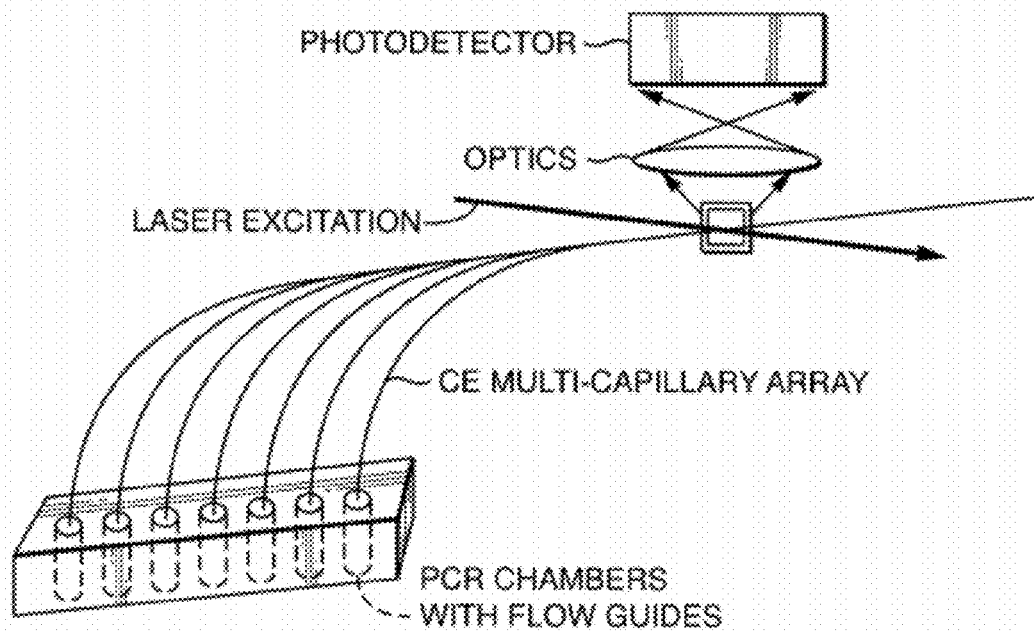
FIG. 9 illustrates a PCR/CE Reactor that is assembled from arrayed capillaries and PCR tubes containing flow guides.
Figure 10A:
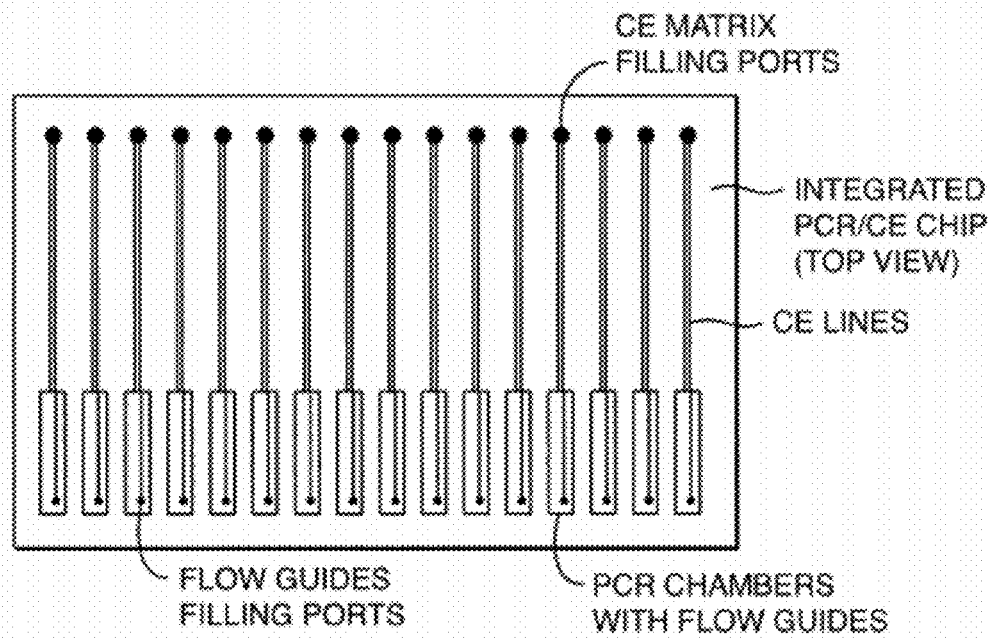
FIG. 10A is a schematic of one embodiment of an integrated PCR/CE array fabricated on chip.
Figure 10B:
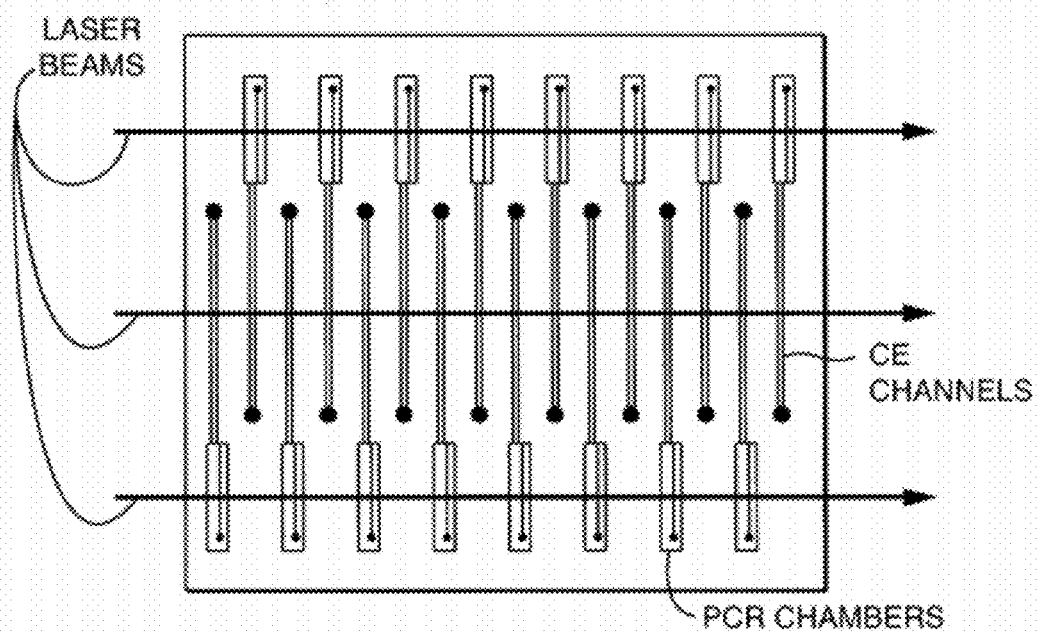
FIG. 10B is a schematic of a second embodiment of an integrated PCR/CE array fabricated on chip.

Particularly preferred embodiments of the claimed device and method comprises an assembly of capillaries (multi-capillary array) or microfabricated chip (glass, silicon, plastic, or a combination there of) used as a vehicle for multi-channel PCR, real-time PCR, PCR-CE, and other applications that involve dispensing, loading, mixing, thermal cycling, separating, etc., of small (microliter, sub-microliter and/or nanoliter) volumes of liquids (e.g., reaction mix, sample). In some embodiments, the device is a PCR processor or reactor comprising PCR chambers, while in other embodiments the device is a PCR processor comprising PCR chambers, as well as an integrated DNA analysis (e.g., CE) component. In some preferred embodiments, the PCR or PCR-CE processor is assembled from capillary tubes (FIG. 9) or microfabricated or carved on a chip (FIG. 10A and FIG. 10B). For real time PCR applications, the processor is used in a horizontal, vertical or inclined position.

I. Loading/Unloading Microfluidic Processors Via One or More Port(s)

This section describes suitable ports or opening for loading (filling) and unloading (sampling) an exemplary PCR or PCR/CE processor (Reactor). These methods are also applicable to other types of microfluidic systems. The channels of the microfluidic processors of the present invention comprise one or more specially designed openings including one or more loading port(s) for filling the channels with different liquids (e.g., DNA/RNA samples or reagent solutions/mixes) as shown in FIG. 4, and FIG. 11A-C. Some channels further comprise one or more auxiliary port(s) for venting air out of the processor, to gain access to stirrers, and/or to gain access to the liquid mixture inside the channels. By this means, reaction products are taken (sampled) from the processor for further analysis or purification. The loading/unloading ports are sealed (with PCR oil, polymer films or layers, or other known methods) to temporarily secure the interior reactor space.

In some embodiments, the unloading port(s) are prefabricated at the distal (bottom/blind) end of the chamber. After the reaction of interest has been completed, a seal is removed to open the port(s). A capillary or a needle is then inserted to withdraw the PCR products from the individual PCR chambers. The unloading port(s) are also used to remove a sample for subsequent analysis with an integrated CE component. The inlet (tip/end portion) of the CE capillary is inserted into the unloading port, and an appropriate voltage is applied between the inlet and a second electrode, causing the sample to enter the inlet of the CE capillary by means of electro-kinetic injection.

Figure 14:
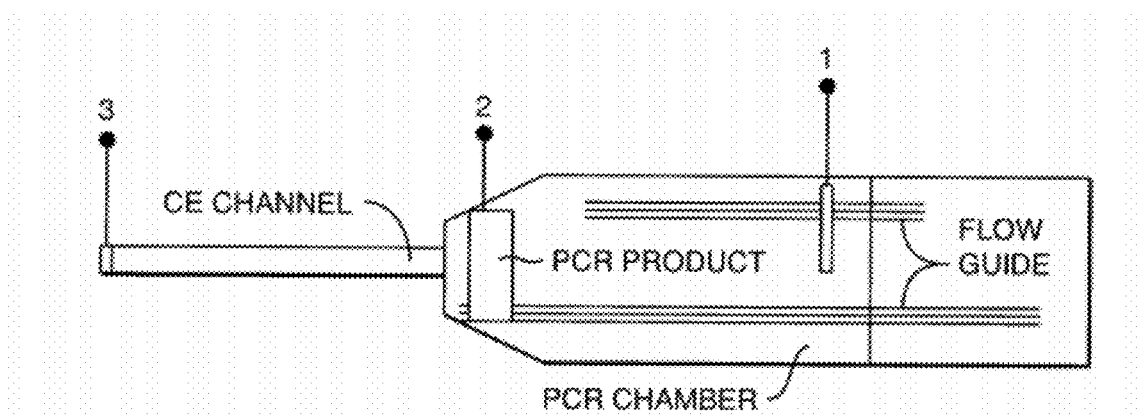
FIG. 14 illustrates the placement of CE electrodes on a PCR/CE chip in one embodiment of the present invention.
Figure 15:
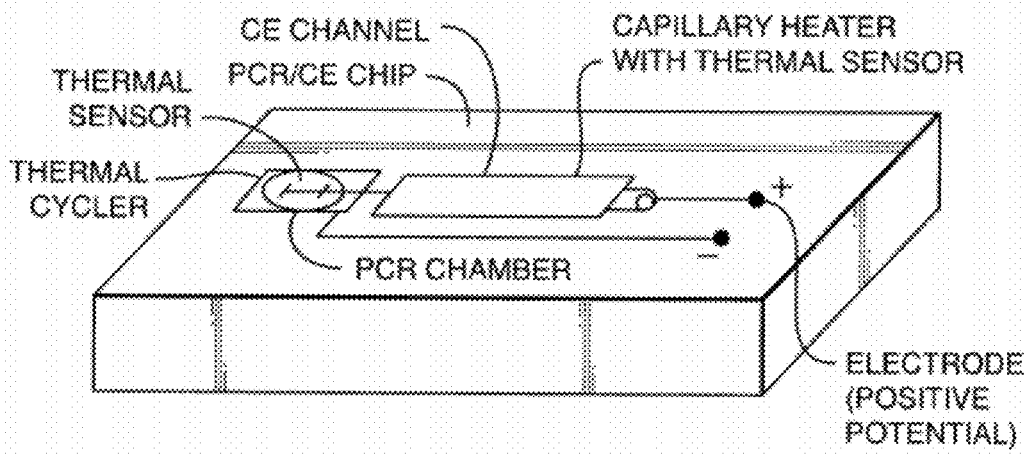
FIG. 15 illustrates a microfluidic system having both thermal cycling means and thermal sensors for performing PCR and CE on a single chip.

Unloading is also performed via loading ports if an additional designated unloading port is undesirable. After thermal cycling has ended, a liquid (e.g., distilled water, buffer, or sequencing reaction mix) is added to the processor chamber such that it is filled beyond the port's opening. Reaction products are then mixed using alternating DC voltage pulses applied between prefabricated electrodes (FIG. 14). Either a sampling or a CE capillary is inserted into the port. In some embodiments, the sampling/CE capillary is tight-fitted into the port. Reaction products are drawn out via sampling capillary, or are electro-kinetically injected into the inlet of the CE capillary.

Figure 11A:
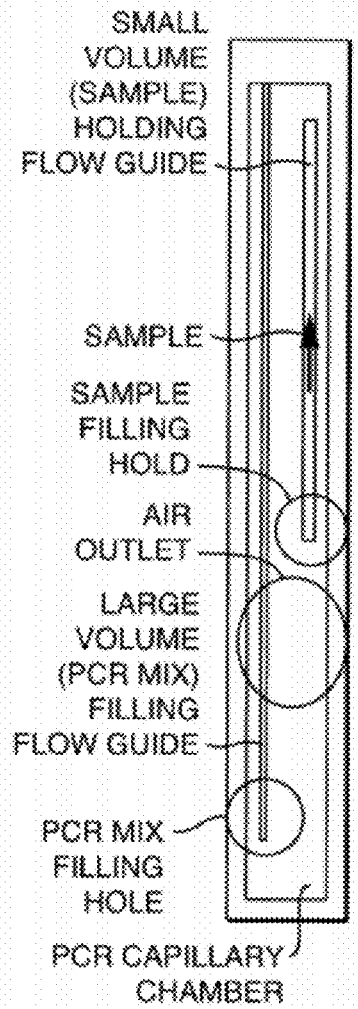
FIG. 11A-C illustrates the filling of a microfluidic chamber with two liquids via two flow guides.
Figure 16:
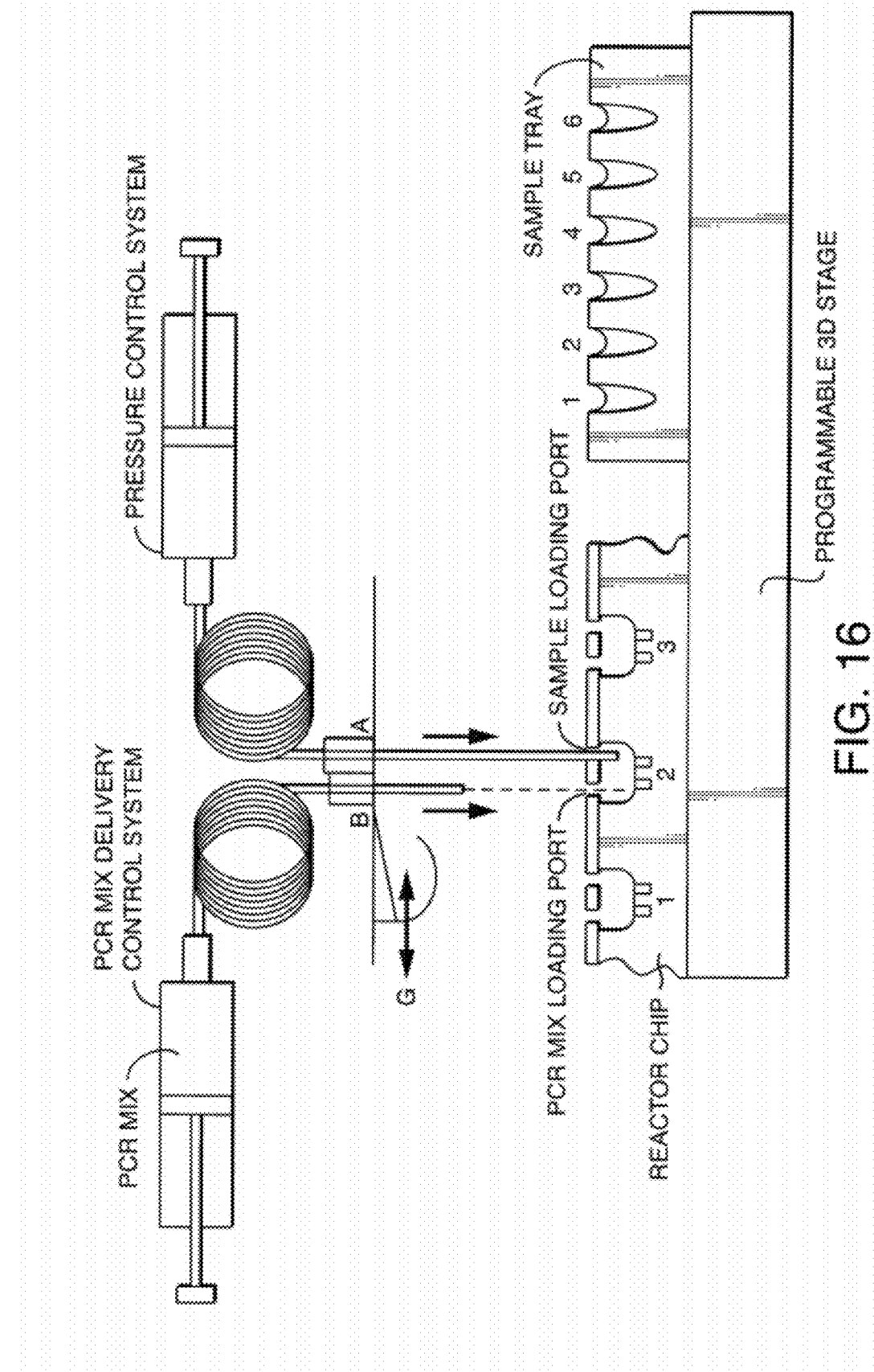
FIG. 16 illustrates a loading station for introduction of reagents (e.g., PCR mix) and a sample into the microfluidic vessels of the present invention.

It is contemplated that through use of the designated sequence of steps for loading a microfluidic processor, cross-contamination between channels, as well as contamination of stock reagents is prevented. This, in turn permits loading tools for stock reagents to be reused (FIG. 11A and FIG. 16). In embodiments in which reaction components are mixed prior to loading, the microfluidic reactor chamber can be filled via one port and one flow guide. Alternatively, in embodiments in which two or more liquids are mixed simultaneously inside the reactor chamber, they can be loaded through the same port and flow guide in series (one after another). In this case, liquids fill the chamber in layers, however, and diffusion between these layers may be a negative factor.

In preferred embodiments, the homogeneity of the mixture in the chamber is ensured via special design of the flow guides and through use of particular filling procedures (FIG. 2B, and FIG. 11A-C). Two functional types of flow guides are provided by the present invention. One type of flow guide termed a holding flow guide, does not contact the microfluidic chamber's distal walls. This type of flow guide is designed to hold a small volume liquid component (SMLC) in place through the flow guide's own capillarity. By varying the profile geometry along such a flow guide, one can vary both the total amount of a liquid held there, and the distribution of the liquid within the chamber. Specifically, when the profile of the guide is uniform, the liquid is distributed evenly along the guide. Alternatively, when the profile of the guide is non-uniform (wider or narrower at certain points or lengths), the bulk of the liquid is held at a discrete region within the chamber (FIG. 2B). The second type of flow guide termed a releasing flow guide makes contact with one of the distal walls of the chamber for delivery of liquid to an end of the chamber (FIG. 2B). When the liquid contacts the wall of the chamber, it starts filling the chamber as a property of the chamber's capillarity, thereby permitting the controlled bubble-free filling of the microfluidic chamber.

Figure 11B:
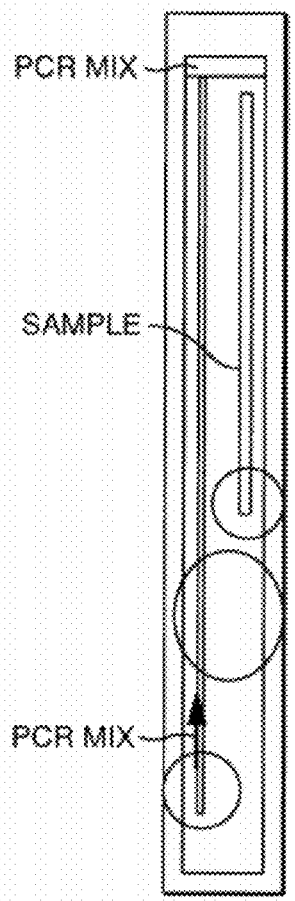
Figure 11C:
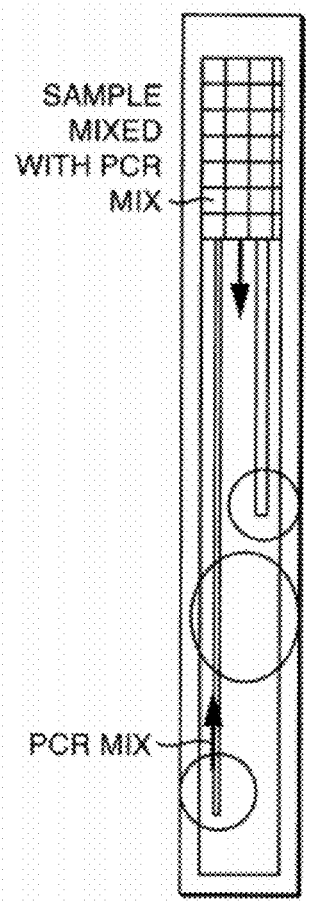
Figure 12:
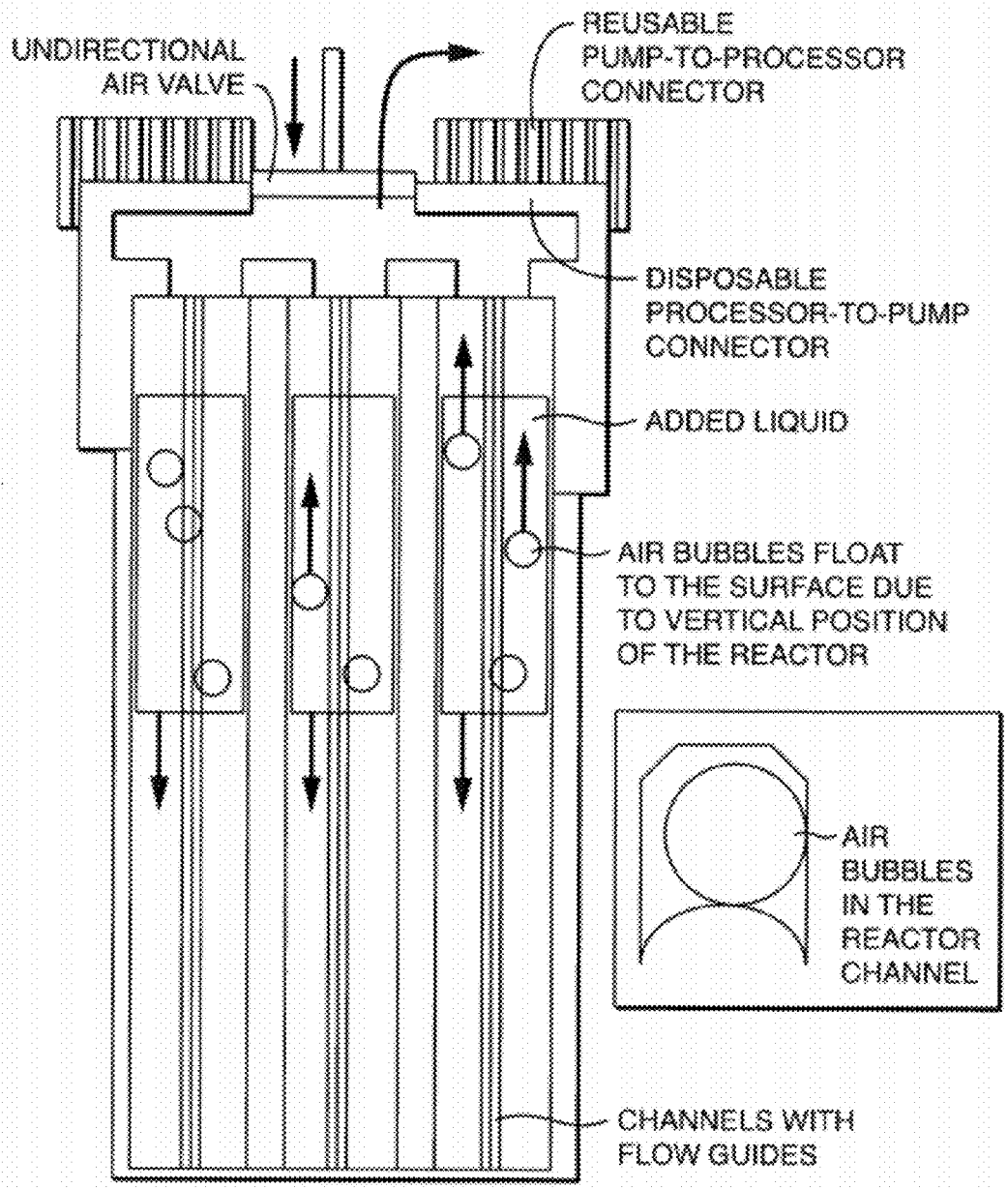
FIG. 12 is a schematic showing the filling of reactor chambers or channels by combining flow guide and pumping techniques.
Figure 13:
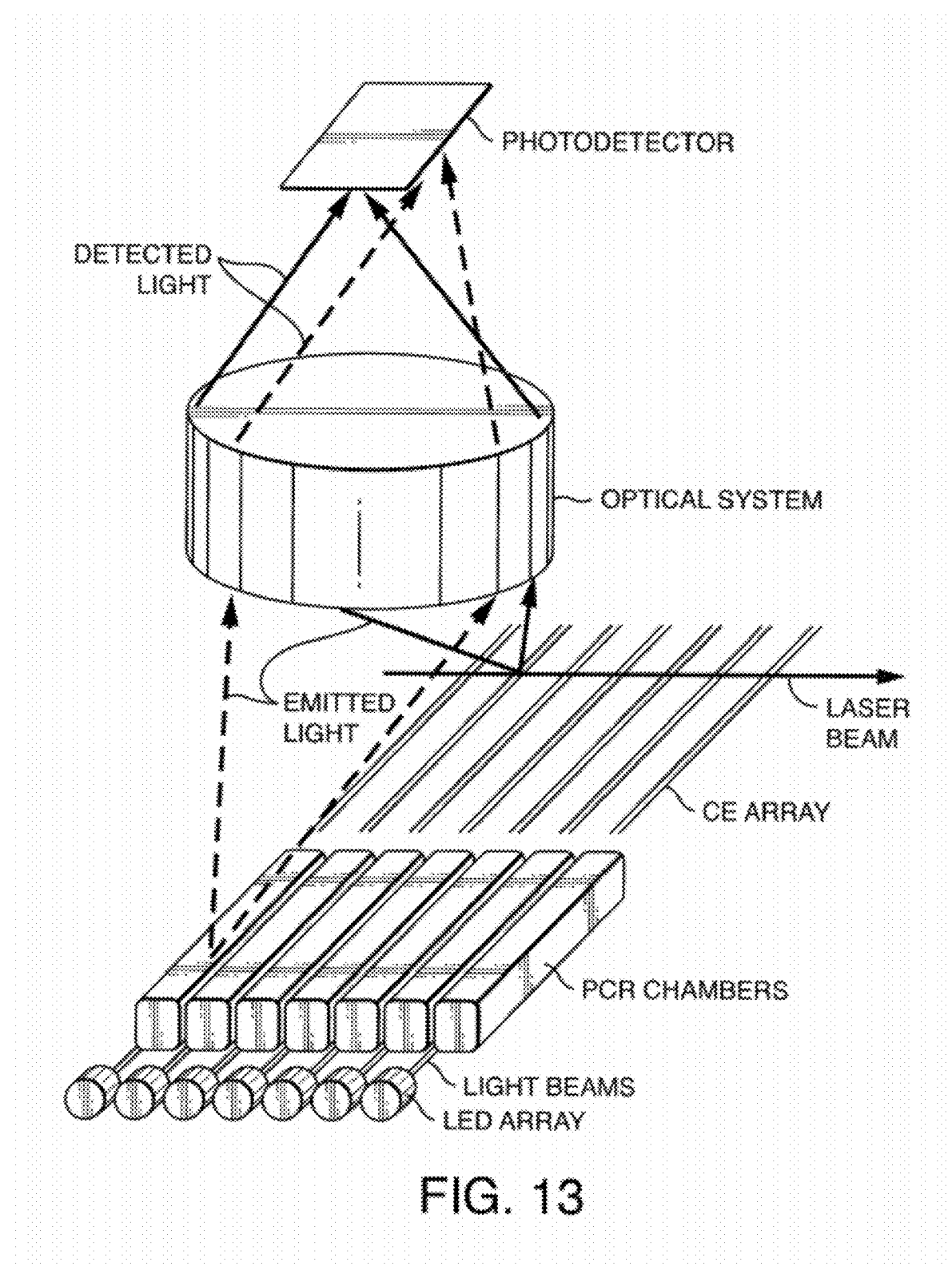
FIG. 13 is a schematic of a microfluidic system having real time PCR and sequence detection components.

Small volume liquid components (SMLC) such as samples are loaded first and are confined within their designated holding flow guide(s) down the length of the reactor chamber (FIG. 11A). In some embodiments, there are several such holding flow guides when several liquids are to be mixed within the chamber. To mix the liquid components within the chamber, the filling procedure is concluded with the loading of a large volume liquid component (LVLC) such as a PCR mix or a solvent via a second loading port onto a releasing flow guide (FIG. 11B). The LVLC fills the reactor chamber from its distant end, and mixes with the SVLC held by the holding flow guide (FIG. 11C). Any additional liquid component(s) (e.g., sequencing reaction mix) that must be added and mixed at a later time during sample preparation or reaction analysis, are loaded onto the releasing hold guide. However, such a procedure results in the filling of the chamber in layers.

II. Improved Mixing of Liquids within a Microfluidic Chamber

In some embodiments when it is necessary to add a third liquid to the chamber containing the reagent-sample mix, air is pumped (using either vibration by bass membrane or micropump) in and out through a special port located at an end of the chamber. By moving the liquid column along the chamber walls, the third liquid mixes by virtue of the interaction of the liquid components with the chamber walls. During PCR process, the air port is sealed.

Alternatively an additional chamber with its own releasing flow guide is prefabricated parallel to the main reactor chamber and separated from the latter by a thin wall, having appropriate dimensions for lining up the latter component along the first reactor mixture. This additional chamber is filled separately. Then the thin separating wall is cracked open by use of resonance sound (e.g., ultrasound gun, irradiated from above or below the chip). In related embodiments, the wall is controlled by application of a signal (e.g., voltage to a piezo crystal), so that it vibrates, bends, curves or shrinks, thus permitting the mixing of the liquids. In still further embodiments, the thin wall is porous with hydrophobic insides. The first reactor mixture stays confined within the main reactor chamber. After the reaction of interest has completed, the additional chamber is filled. Liquids in both chambers bridge the pores, collapse, and start mixing by diffusion. In some embodiments a puff of air is added to push the latter component out of its chamber and through the pores (e.g., when the thin wall contains a tight port).

In still further embodiments, the third liquid (latter component such as a DNA sequencing mix) is loaded on top of the reagent-sample mix. Subsequently, the negatively charged DNA molecules are moved around the chamber by using alternating DC current pulses.

Moreover, in some embodiments a stirrer is either prefabricated inside the chamber in the form of a filament or straw attached only at the proximal end (near the loading ports) or inserted into the cavity through an opening at an end of the chamber. Suitable stirring straws include but are not limited to those made of electro-controlled materials, magnetic materials, and glass or silicon. Stirring straws made from electro-controlled materials (piezo crystal, bi-metal, etc.) bend under voltage or current, applied by electrodes extended outside the chamber. Application of alternating signals to the electrodes causes the straw to stir and mix the liquids. Stirring straws with cores made from a magnetic material stir and mix the liquids when a vibrating magnet probe is brought near the chamber. Similarly, stirring straws made from glass or silicon by etching, and having an opening above the straw stir and mix the liquids when a vibrating probe is inserted through the opening.

Microfluidic channels can also be filled with multiple liquids sequentially, when the channels comprise flow guide(s) with multiple holding/exchange areas, as shown in FIG. 3N.

III. Mixing of Reaction Components During Reactions

It is preferable to mix reagents well before and during reaction(s). One solution for mixing the reaction during incubation or thermal cycling is through the use of prefabricated stirrers attached to the inside of the chambers as described above. Alternatively, nano- or micro-stirrers made from cut nano- or micro-tubes or bars by known processes are employed. The stirrers are given a magnetic or an electric dipole and fed into the chamber along with the various liquids. Once the chamber is filled, nano- or micro-tubes are stirred remotely by applying controlled alternating pulses of magnetic or electric fields via induction coil or capacitor, respectively. The latter is prefabricated on the microfluidic chip or part of the instrument that handles the microfluidic chip. In some embodiments, the stirring action continues during all of the PCR cycles, thereby accelerating the process. In addition, since in small volumes surface effects become more prominent because of the dramatic increases in surface to volume ratio, continuous stirring is contemplated to compensate for or neutralize the negative effects caused for instance by non-uniformities in surface tension, profile geometry and diffusion, or chemical and electro-static effects on glass surfaces.

IV. Using a Capillary Reactor as Genomic Multi-Array Tool for Diagnostics

In genomics (hybridization arrays, hybridization assays), multiple nucleic acid probes are attached to chips during pre-fabrication. In some embodiments, the inventors contemplate the attachment of multiple primers (e.g., several thousand primers for known gene markers of human and/or animal cancers) to the inner surfaces of microfluidic capillary chambers during their prefabrication. In some embodiments, a single probe (or primer) is attached to each chamber, while in other embodiments, the probes are attached in stripes on each chamber, and coded accordingly. Then the chip or assembly containing the microfluidic capillary chambers is filled with both PCR reaction mix and sample from a patient for performing real-time PCR (and subsequent analysis). It is contemplated that such chips and instruments will be routinely used as an on-bench diagnostic tool in various clinics.

V. Automated Precision Loading of Liquids Into Microfluidic Devices

An important factor that limits development of micro-, submicro-, or nanoscale PCR is the step of loading of micro-, sub-micro-, or nanoliter volumes of samples and reagents into capillary chambers via small (10-300 μm diameter) openings or ports. Manual pipetting of sub-microliter volumes is inaccurate and lacks reproducibility, and is prone to spills, and contamination of samples and stock solutions, as well as other human errors. However, existing robotic loading stations are unsatisfactory (e.g., complex, cumbersome, and expensive). Thus what is needed in the art are robotic loading stations that are integrated with a PCR machine, and which use disposable tips (as opposed to dispenser washouts).

The present invention solves these problems by loading (and unloading) liquids via flexible capillary tubes, followed by the disposal of the used portion of the capillary tubes after each dispensing/withdrawing step (FIG. 16). For convenience, the flexible capillary tube is stored coiled (e.g., on a bobbin). The microfluidic reactor array and a sample tray move on top of a three-dimensional, programmable stage, while the companion loading unit is stationary.

VI. Real time PCR and Sequencing Detection Systems

There are a variety of optical systems and photodetectors that can be used for detection of PCR products or other CE separated molecules on the PCR-CE chips of the present invention. Suitable optical systems can separately illuminate individual PCR chambers and/or CE channels by using one or several light sources (e.g., lasers, LEDs), or can illuminate several PCR chambers (or CE channels) simultaneously.

In some embodiments, the optical detection system is based on open optics, while in other embodiments, fiber optics or both open and fiber optics features are utilized. Detection of different channels (and different chambers) can be done in a multiplex mode or simultaneously. When detection is carried out simultaneously either multi-pixel photodetectors or single pixel detectors are used. However, if a single pixel detector is employed, illumination of individual PCR chambers and/or individual CE channels must be done with multiple light sources with encoded output power.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); PCR (polymerase chain reaction); and CE (capillary electrophoresis); SVLC (small volume liquid component); and LVLC (large volume liquid component).

Example 1

Bubble-less Loading of Two Liquids in a Chamber with Dual Flow Guides

Figure 17:
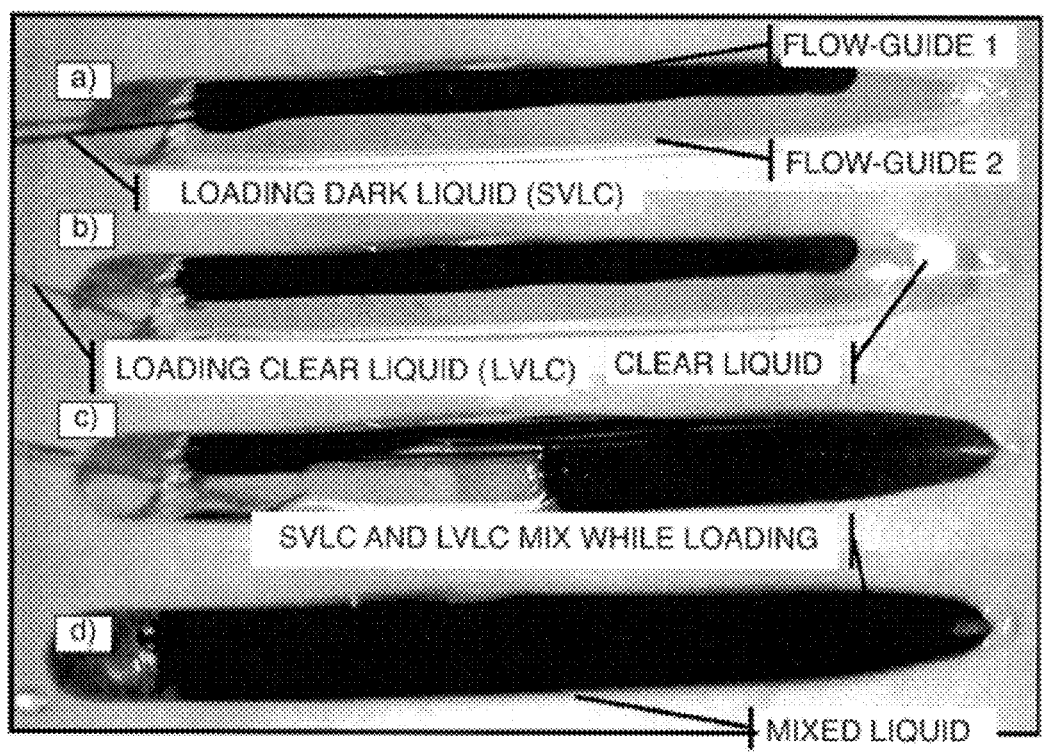
FIG. 17 depicts the loading of two liquids into a glass chamber comprising both a holding flow guide and a releasing flow guide.

During development of the present invention, a glass chamber containing two flow guides has been successfully fabricated as shown in FIG. 17. A first flow (holding) guide was made of a thin glass capillary, such that it did not touch the distal chamber wall. This configuration permitted the use of the flow guide for holding a small volume liquid component (SVLC). A second flow guide also made of a thin glass capillary, and designed to touch the distal chamber wall, was used for the bubble-less filling of the chamber with a large volume liquid component (LVLC). As contemplated by the inventors, a mixing of the LVLC and SVLC was observed to occur along the length of the holding flow guide while the LVLC was moving towards the chamber inlet. The mixing was clearly visualized during testing through use of a dark blue SVLC and a clear LVLC.

Example 2

Bubble-less Loading of Two Liquids in a Chamber with a Single Flow Guide

Figure 18:
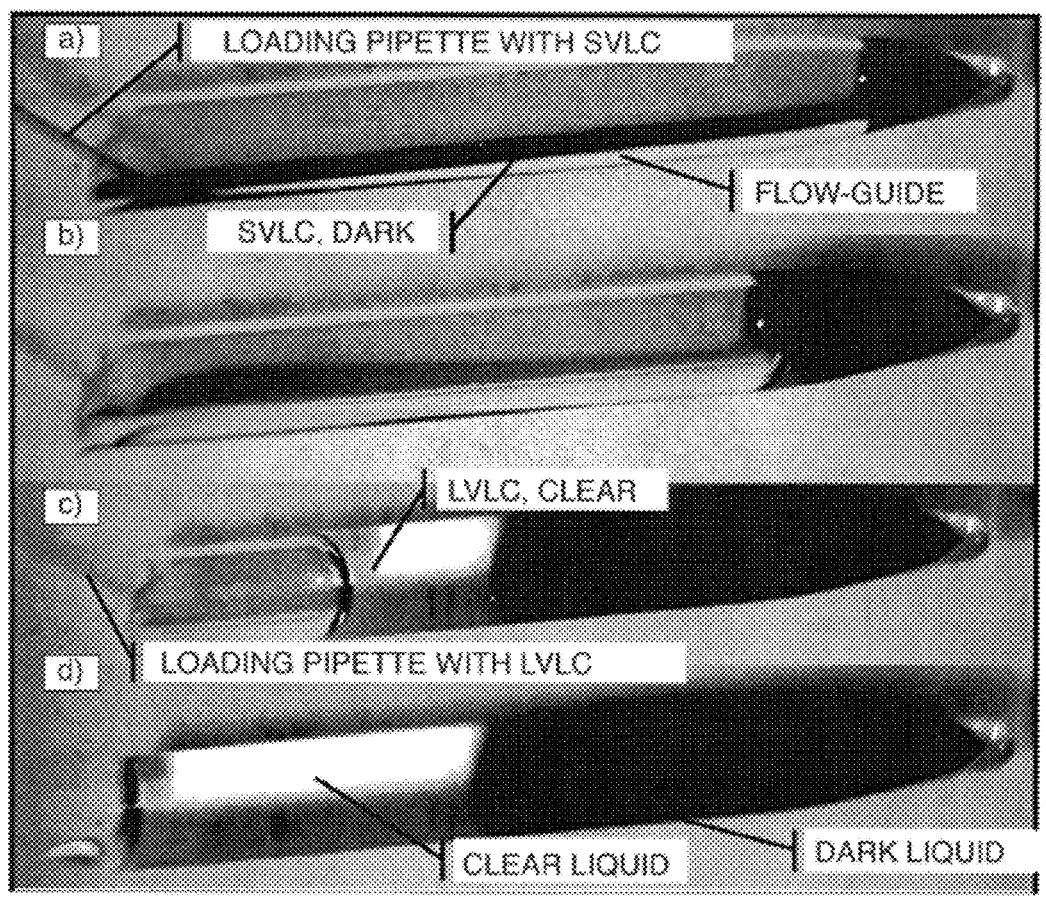
FIG. 18 depicts the loading of two liquids into a glass chamber comprising a single (releasing) flow guide.

During development of the present invention, a glass chamber containing a single flow guide made of a thin glass capillary, has been successfully fabricated as shown in FIG. 18. The flow guide is attached to the chamber's wall extends from below the loading port to the distal chamber wall. The SVLC (dark liquid) was loaded first, followed by the LVLC (clear liquid). The SVLV and LVLC filled the chamber in layers in the absence of bubble introduction, and without mixing of the two liquids. Even after 90 minutes, the SVLC and LVLC were not observed to form a homogeneous solution.

Example 3

Automated Loading of Liquids Into Microfluidic Devices

This example describes improved methods for the automated loading of microfluidic devices with the use of a stationary loading station and a movable stage as depicted in FIG. 16. To begin with, the stage is used to position the sample tray so that sample well 1 is under a first (sample) loading capillary tube (A in FIG. 16). The sample-loading capillary is pushed downward to sample 1 for a measured distance. The stage is then raised so that sample solution 1 in the sample tray is in contact with the sample-loading capillary tube, which is filled with sample 1 (preferably by capillary force). Precise timing of a pressure control system is used to withdraw an exact volume of the sample in the capillary (to ensure accuracy a calibration step can be employed). The stage is then lowered and positioned so that the sample-loading port of the $1^{st}$ PCR/reactor chamber is aligned with the sample-loading capillary, which is then projecting into the chamber through the loading port above a first flow guide (e.g., holding flow guide). At this position, the second, reagent-loading (PCR mix) capillary (B in FIG. 16) projects into the chamber through a loading port above a second flow guide (e.g., releasing flow guide). As the stage is caused to ascend, the sample-loading capillary gently touches the floor of PCR/reactor chamber atop the first/holding (SVLC) flow guide. The sample is dispensed from the sample-loading capillary onto the holding flow guide by a slow air puff from a pressure control device. The reagent-loading capillary is pushed/protruded downward to gently touch the floor of PCR/reactor chamber atop the second/releasing (LVLC) flow guide. The required PCR mix (or other reaction cocktail) volume is slowly dispensed from the reagent-loading capillary onto the releasing flow guide by precise action of PCR mix delivery control system. The reactor chamber is filled via this flow guide resulting in the mixture of the two liquids. The stage is then lowered, and a guillotine (G in FIG. 16) cleaves off (lops) the used portions of both the sample-loading and reagent-loading capillaries into a collector. The sequence of steps in then repeated until all chambers of the PCR reactor are loaded with sample and reagent.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields, are intended to be within the scope of the following claims.

We claim:

1. A microfluidic device comprising one or more microfluidic vessel(s), wherein said microfluidic vessel(s) comprise(s) (i) a sample deposition port, and (ii) walls comprising flow-guides contained therein, said flow-guides having pre-determined capillarities, wherein said flow-guides comprise:
    a) a holding flow-guide configured such that its capillarity confines a sample deposited in said holding flow-guide within said holding flow guide such that said sample does not touch the rest of said vessel, wherein said holding flow-guide extends from said port toward a distal wall of said vessel but does not contact said wall, and
    b) a releasing flow-guide configured such that its capillarity confines a reagent mixture deposited therein such that said mixture touches the rest of said vessel first at said distal wall of said vessel, wherein said releasing flow-guide extends from said deposition port to said distal wall of said vessel.

2. The microfluidic device of claim 1, wherein said holding flow-guide comprises an area within said microfluidic vessel(s) having reduced capillarity.

3. The microfluidic device of claim 1, wherein said holding flow-guide comprises areas within said microfluidic vessel(s) having enhanced capillarity.

4. The microfluidic device of claim 1, wherein said holding flow-guide comprises areas within said microfluidic vessel(s) having reduced capillarity, and an area within said vessel(s) having enhanced capillarity.

5. The microfluidic device of claim 1, wherein said holding flow-guide is a structural flow-guide.

6. The microfluidic device of claim 1, wherein said holding flow-guide is a surface flow-guide.

7. The microfluidic device of claim 1, wherein said holding flow-guide is a hybrid structural/surface flow-guide.

8. The microfluidic device of claim 1, wherein said releasing flow-guide comprises an area within said microfluidic vessel(s) having reduced capillarity.

9. The microfluidic device of claim 1, wherein said releasing flow-guide comprises areas within said microfluidic vessel(s) having enhanced capillarity.

10. The microfluidic device of claim 1, wherein said releasing flow-guide comprises areas within said microfluidic vessel(s) having reduced capillarity, and an area within said vessel(s) having enhanced capillarity.

11. The microfluidic device of claim 1, wherein said releasing flow-guide is a structural flow-guide.

12. The microfluidic device of claim 1, wherein said releasing flow-guide is a surface flow-guide.

13. The microfluidic device of claim 12, wherein said surface flow-guide comprises a hydrophobic material deposited within said microfluidic vessel(s).

* * * * *